United States Patent
Hosoi et al.

(10) Patent No.: US 10,604,562 B2
(45) Date of Patent: Mar. 31, 2020

(54) ANTI-TRANSTHYRETIN HUMANIZED ANTIBODY

(71) Applicants: KM BIOLOGICS CO., LTD., Kumamoto (JP); NATIONAL UNIVERSITY CORPORATION KUMAMOTO UNIVERSITY, Kumamoto (JP)

(72) Inventors: Akihiko Hosoi, Kumamoto (JP); Masaharu Torikai, Kumamoto (JP); Tomoyo Takeo, Kumamoto (JP); Masayo Ueno, Kumamoto (JP); Hirofumi Higuchi, Kikuchi (JP); Kenji Soejima, Kumamoto (JP); Toshihiro Nakashima, Kumamoto (JP); Yukio Ando, Kumamoto (JP); Hirofumi Jono, Kumamoto (JP); Yu Su, Shanghai (CN)

(73) Assignees: KM BIOLOGICS CO., LTD., Kumamoto (JP); NATIONAL UNIVERSITY CORPORATION KUMAMOTO UNIVERSITY, Kumamoto (JP)

( * ) Notice: Subject to any disclaimer, the term of this patent is extended or adjusted under 35 U.S.C. 154(b) by 0 days.

(21) Appl. No.: 15/114,600

(22) PCT Filed: Jan. 23, 2015

(86) PCT No.: PCT/JP2015/051856
§ 371 (c)(1),
(2) Date: Jul. 27, 2016

(87) PCT Pub. No.: WO2015/115331
PCT Pub. Date: Aug. 6, 2015

(65) Prior Publication Data
US 2016/0347832 A1   Dec. 1, 2016

(30) Foreign Application Priority Data

Jan. 29, 2014 (JP) ................... 2014-014911

(51) Int. Cl.
| C07K 16/18 | (2006.01) |
| A61K 39/395 | (2006.01) |
| G01N 33/68 | (2006.01) |
| A61K 39/00 | (2006.01) |
| C07K 14/00 | (2006.01) |

(52) U.S. Cl.
CPC .......... *C07K 16/18* (2013.01); *A61K 39/0007* (2013.01); *G01N 33/6896* (2013.01); *A61K 2039/505* (2013.01); *C07K 14/00* (2013.01); *C07K 2317/24* (2013.01); *C07K 2317/34* (2013.01); *C07K 2317/51* (2013.01); *C07K 2317/515* (2013.01); *C07K 2317/565* (2013.01); *C07K 2317/622* (2013.01); *C07K 2317/76* (2013.01); *C07K 2317/92* (2013.01); *G01N 2333/47* (2013.01); *G01N 2800/28* (2013.01); *G01N 2800/7047* (2013.01)

(58) Field of Classification Search
CPC ................ A61K 39/0007; C07K 16/18; C07K 2317/21; C07K 2317/565; C07K 14/00
See application file for complete search history.

(56) References Cited

U.S. PATENT DOCUMENTS

| 7,601,351 B1 | 10/2009 | Rosen et al. |
| 2004/0151721 A1 | 8/2004 | O'Keefe et al. |
| 2005/0164365 A1 | 7/2005 | Yonemura et al. |
| 2008/0153132 A1 | 6/2008 | Yonemura et al. |
| 2014/0056904 A1 | 2/2014 | Chakrabartty et al. |

FOREIGN PATENT DOCUMENTS

| JP | 2010-195710 | 9/2010 |
| WO | 03/004647 | 1/2003 |
| WO | 2009/055054 | 4/2009 |
| WO | 2009/086539 | 7/2009 |
| WO | 2010/030203 | 3/2010 |
| WO | 2013/126810 | 8/2013 |
| WO | 2014/124334 | 8/2014 |

OTHER PUBLICATIONS

Foote et al., J. Mol. Biol. 224 (1992): 487-499.*
Phay et al., "Transthyretin Aggregate-Specific Antibodies Recognize Cryptic Epitopes on Patient-Derived Amyloid Fibrils", Rejuvenation Research, 17(2):97-104 (2014).
Su et al., "Antibody therapy for familial amyloidotic polyneuropathy", Amyloid, 19(S1):45-46 (2012).
Gustavsson et al., "Mechanisms of Transthyretin Amyloidogenesis. Antigenic Mapping of Transthyretin Purified from Plasma and Amyloid Fibrils and within in Situ Tissue Localizations", American Journal of Pathology, 144(6):1301-1311 (1994).
Léger et al., "Humanization of Antibodies", Molecular Medicine and Medical Chemistry, pp. 1-23 (2011).
Almagro et al., "Humanization of Antibodies", Frontiers in Bioscience, Albertson, NY, US, 13:1619-1633 (2008).
Little, "Chapter 7—Therapeutic Antibodies from XenoMouse Transgenic Mice" from "Recombinant Antibodies for Immunotherapy", Cambridge University Press, Cambridge, UK, pp. 89-107 (2009).
Lonberg, "Human antibodies from transgenic animals", Nature Biotechnology, 23(9):1117-1125 (2005).
Hoogenboom, "Selecting and screening recombinant antibody libraries", Nature Biotechnology, 23(9):1105-1116 (2005).

(Continued)

*Primary Examiner* — Robert C Hayes
(74) *Attorney, Agent, or Firm* — Wenderoth, Lind & Ponack, L.L.P.

(57) ABSTRACT

A humanized antibody which comprises a complementarity determining region of an H chain consisting of the amino acid sequence as shown in SEQ ID NOs: 1 to 3 and a complementarity determining region of an L chain consisting of the amino acid sequence as shown in SEQ ID NOs: 4 to 6. The humanized antibody of the present invention has the activity to specifically bind to transthyretin (TTR) with structural change and the activity to inhibit fibrillization of TTR and is a humanized antibody suitable for application to human body.

16 Claims, 9 Drawing Sheets

Specification includes a Sequence Listing.

(56) References Cited

OTHER PUBLICATIONS

Matsubara et al., "Dimeric Transthyretin Variant Assembles into Spherical Neurotoxins", Biochemistry, 44:3280-3288 (2005).
Extended European Search Report dated May 26, 2017 in corresponding European Application No. 15743230.3.
International Search Report dated Apr. 14, 2015 in International (PCT) Application No. PCT/JP2015/051860.
International Preliminary Report on Patentability dated Aug. 2, 2016 in International (PCT) Application No. PCT/JP2015/051860.
Partial Supplementary European Search Report dated May 31, 2017 in European Application No. 15743541.3.
International Search Report dated Apr. 14, 2015 in International Application No. PCT/JP2015/051856.
International Preliminary Report on Patentability dated Aug. 2, 2016 in International Application No. PCT/JP2015/051856.
George C. Glenner, M.D., Medical Progress, "Amyloid Deposits and Amyloidosis" The β-Fibrilloses, N. Engl J Med, vol. 302, No. 24, 1333-1343, 1980.
Yukio Ando, MD et al., "Pathogenesis and Therapy for Transthyretin Related Amyloidosis", Rinsho Byori, 56, 114-120, 2008 with English abstract.
Yoshiki Sekijima et al., "Molecular pathogenesis of TTR amyloidosis and its inhibition", Igaku-No-Ayumi, 229, 349-356, 2009 with partial English translation.
Yuko Kato-Motozaki et al., "Molecular epidemiology of familial amyloid polyneuropathy", Igaku-No-Ayumi, 229, 357-362, 2009 with partial English translation.
Xu Hou et al., "Transthyretin and familial amyloidotic polyneuropathy" Recent progress in understanding the molecular mechanism of neurodegeneration, FEBS J, 274, 1637-1650, 2007.
Shukuro Araki et al., Transthyretin-related familial amyloidotic polyneuropathy—Progress in Kumamoto, Japan (1967-2010) -, Proc. Jpn. Acad., Ser. B Phys Biol Sci, 86, 694-706, 2010.
Vasso Episkopou et al., "Disruption of the transthyretin gene results in mice with depressed levels of plasma retinol and thyroid hormone", Proc Natl Acad Sci USA, 90, 2375-2379, 1993.
Yukio Ando, "Liver transplantation and other therapies for familial amyloidotic polyneuropathy", Igaku-No-Ayumi, 229, 363-368, 2009 with partial English translation, Abstract only.
Gerard Said et al., "Tafamidis", Nat Rev Drug Discov, 11, 185-186, 2012.
Gundars Goldsteins et al., "Exposure of cryptic epitopes on transthyretin only in amyloid and in amyloidogenic mutants", Proc Natl Acad Sci USA, 96, 3108-3113, 1999.
Hisayasu Terazaki et al., "Immunization in familial amyloidotic polyneuropathy: counteracting deposition by immunization with a Y78F TTR mutant", Lab Invest, 86, 23-31, 2006.
Joakim Bergstrom et al., "Surface exposed epitopes and structural heterogeneity of in vivo formed transthyretin amyloid fibrils", Biochem Biophys Res Commun, 348, 532-539, 2006.
Kimiaki Matsubara et al., "Expression of a synthetic gene encoding human transthyretin in *Escherichia coli*", Protein Expr Purif, 30, 55-61, 2003.
Mitsuharu Ueda et al., "A transgenic rat with the human ATTR V30M: A Novel Tool for analyses of ATTR metabolisms", Biochem Biophys Res Commun, 352, 299-304, 2007.
S. Senju et al., "Generation of dendritic cells and macrophages from human induced pluripotent stem cells aiming at cell therapy", Gene Therapy, 18, 874-883, 2011.
Akihiko Hosoi, "Antibody Therapy for Familial Amyloidotic Polyneuropathy", Reimei, Oct. 1, 2012, vol. 21, pp. 47-51 with partial English translation, Abstract Only.
M. Ueda et al., Iyaku (Medicine and Drug) Journal, 2012, vol. 48, No. 5, pp. 1307-1314 with partial English translation, Abstract Only.
Y. Ando et al., Annual Review Shinkei (Nerve) 2011, pp. 310-317 with partial English translation, Abstract only.
H. Oba et al., Frontier of Development of Antibody Medicine, Jul. 20, 2007, pp. 157-169 with partial English translation, Abstract only.
Extended European Search Report dated Aug. 14, 2017 in corresponding European patent application No. 15743541.3.
G. Arsequell et al., Methods to Evaluate the Inhibition of TTR Fibrillogenesis Induced by Small Ligands, Current Medicinal Chemistry: The New International Journal for Timely In-Depth Reviews in Medicinal Chemistry, vol. 19, No. 15, Apr. 24, 2012, pp. 2343-2355.
Ignacio Dolado et al., Kinetic Assay for High-Throughput Screening of In Vitro Transthyretin Amyloid Fibrillogenesis Inhibitors, Journal of Combinatorial Chemistry, vol. 7, No. 2, Mar. 1, 2005, pp. 246-252.
Ricardo Sant'Anna et al., Inhibition of Human Transthyretin Aggregation by Non-Steroidal Anti-Inflammatory Compounds: A Structural and Thermodynamic Analysis, International Journal of Molecular Sciences, vol. 14, No. 3, Mar. 6, 2013, pp. 5284-5311.
Reixach N et al., Cell based screening inhibitors of transthyretin aggregation, Biochemical and Biophysical Research Communications, Elsevier, Amsterdam, NL, vol. 348, No. 3, Sep. 29, 2006, pp. 889-897.
Chinese Office Action dated Sep. 25, 2018 in corresponding Chinese Application No. 201580017230.1, with English translation.
Office Action dated Jun. 26, 2018 issued in European patent application No. 15743230.3.
Office Action dated Aug. 20, 2018 issued in European patent application No. 15743541.3.

\* cited by examiner

*: p =0.0271

```
SEQUENCE LISTING

<160> NUMBER OF SEQ ID NOS: 24

<210> SEQ ID NO 1
<211> LENGTH: 5
<212> TYPE: PRT
<213> ORGANISM: Mouse

<400> SEQUENCE: 1

Arg Tyr Trp Ile Thr
1               5

<210> SEQ ID NO 2
<211> LENGTH: 17
<212> TYPE: PRT
<213> ORGANISM: Mouse

<400> SEQUENCE: 2

Asp Ile Tyr Pro Gly Ser Gly Arg Thr Asn Tyr Asn Glu Lys Phe Lys
1               5                   10                  15

Asn

<210> SEQ ID NO 3
<211> LENGTH: 9
<212> TYPE: PRT
<213> ORGANISM: Mouse

<400> SEQUENCE: 3

Tyr Tyr Gly Ser Thr Tyr Phe Tyr Val
1               5

<210> SEQ ID NO 4
<211> LENGTH: 16
<212> TYPE: PRT
<213> ORGANISM: Mouse

<400> SEQUENCE: 4

Arg Ser Ser Lys Ser Leu Leu Tyr Lys Asp Gly Lys Thr Tyr Leu Asn
1               5                   10                  15
```

```
<210> SEQ ID NO 5
<211> LENGTH: 7
<212> TYPE: PRT
<213> ORGANISM: Mouse

<400> SEQUENCE: 5

Leu Met Ser Thr Arg Ala Ser
1               5

<210> SEQ ID NO 6
<211> LENGTH: 9
<212> TYPE: PRT
<213> ORGANISM: Mouse

<400> SEQUENCE: 6

Gln Gln Leu Val Glu Tyr Pro Arg Thr
1               5

<210> SEQ ID NO 7
<211> LENGTH: 118
<212> TYPE: PRT
<213> ORGANISM: Artificial
<220> FEATURE:
<223> OTHER INFORMATION: Humanized VH region

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
                20                  25                  30

Trp Ile Thr Trp Val Arg Gln Arg Pro Gly Gln Gly Leu Glu Trp Met
            35                  40                  45

Gly Asp Ile Tyr Pro Gly Ser Gly Arg Thr Asn Tyr Asn Glu Lys Phe
    50                  55                  60

Lys Asn Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Thr Tyr Phe Tyr Val Trp Gly Gln Gly Thr
                100                 105                 110

Thr Val Thr Val Ser Ser
            115

<210> SEQ ID NO 8
<211> LENGTH: 112
<212> TYPE: PRT
<213> ORGANISM: Artificial
<220> FEATURE:
<223> OTHER INFORMATION: Humanized VL region

<400> SEQUENCE: 8

Asp Val Val Met Thr Gln Ser Pro Leu Ser Leu Pro Val Thr Leu Gly
1               5                   10                  15

Gln Pro Ala Ser Ile Ser Cys Arg Ser Ser Lys Ser Leu Leu Tyr Lys
                20                  25                  30

Asp Gly Lys Thr Tyr Leu Asn Trp Phe Gln Gln Arg Pro Gly Gln Ser
            35                  40                  45

Pro Gln Leu Leu Ile Tyr Leu Met Ser Thr Arg Ala Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Val Tyr Tyr Cys Gln Gln Leu
                85                  90                  95

Val Glu Tyr Pro Arg Thr Phe Gly Gly Thr Lys Val Glu Ile Lys
        100                 105                 110

<210> SEQ ID NO 9
<211> LENGTH: 10
<212> TYPE: PRT
<213> ORGANISM: Homo sapiens

<400> SEQUENCE: 9

Ser Tyr Ser Thr Thr Ala Val Val Thr Asn
1               5                   10

<210> SEQ ID NO 10
<211> LENGTH: 47
<212> TYPE: DNA
<213> ORGANISM: Artificial
<220> FEATURE:
<223> OTHER INFORMATION: T24VH-Fw primer

<400> SEQUENCE: 10
tgttgctatt ctcgagggtg tccagtgtca ggtccaactg cagcagc             47

<210> SEQ ID NO 11
<211> LENGTH: 35
<212> TYPE: DNA
<213> ORGANISM: Artificial
<220> FEATURE:
<223> OTHER INFORMATION: T24VH-Rv primer

<400> SEQUENCE: 11
ggggtgtcgt tttcgctgag gagacggtga ccgtg                          35

<210> SEQ ID NO 12
<211> LENGTH: 47
<212> TYPE: DNA
<213> ORGANISM: Artificial
<220> FEATURE:
<223> OTHER INFORMATION: T24VL-Fw primer

<400> SEQUENCE: 12
gggtcccagg ctcgagtggg gaaattgtga taacccagga tgaactc             47

<210> SEQ ID NO 13
<211> LENGTH: 46
<212> TYPE: DNA
<213> ORGANISM: Artificial
<220> FEATURE:
<223> OTHER INFORMATION: T24VL-Rv primer

<400> SEQUENCE: 13
aagcgtattt ggatccactc acgttttatt tccagcttgg tccccc              46

<210> SEQ ID NO 14
<211> LENGTH: 32
<212> TYPE: DNA
<213> ORGANISM: Artificial
<220> FEATURE:
<223> OTHER INFORMATION: pCAG-Fw primer

<400> SEQUENCE: 14
gaccggcggc tctagagcct ctgctaacca tg                             32
```

```
<210> SEQ ID NO 15
<211> LENGTH: 27
<212> TYPE: DNA
<213> ORGANISM: Artificial
<220> FEATURE:
<223> OTHER INFORMATION: TTR-F2 primer

<400> SEQUENCE: 15
cgcggatccg gccctacggg caccggt                                        27

<210> SEQ ID NO 16
<211> LENGTH: 36
<212> TYPE: DNA
<213> ORGANISM: Artificial
<220> FEATURE:
<223> OTHER INFORMATION: TTR-R primer

<400> SEQUENCE: 16
cccaagcttt tatcattcct tgggattggt gacgac                              36

<210> SEQ ID NO 17
<211> LENGTH: 15
<212> TYPE: DNA
<213> ORGANISM: Mouse

<400> SEQUENCE: 17
aggtactgga taacc                                                     15

<210> SEQ ID NO 18
<211> LENGTH: 51
<212> TYPE: DNA
<213> ORGANISM: Mouse

<400> SEQUENCE: 18
gatatttatc ctggtagtgg tagaactaat tacaatgaga agttcaagaa c             51

<210> SEQ ID NO 19
<211> LENGTH: 27
<212> TYPE: DNA
<213> ORGANISM: Mouse

<400> SEQUENCE: 19
tactacggta gtacctactt ctatgtc                                        27

<210> SEQ ID NO 20
<211> LENGTH: 48
<212> TYPE: DNA
<213> ORGANISM: Mouse

<400> SEQUENCE: 20
aggtctagta agagtctcct gtataaggac gggaagacat acttgaat                 48

<210> SEQ ID NO 21
<211> LENGTH: 21
<212> TYPE: DNA
<213> ORGANISM: Mouse

<400> SEQUENCE: 21
ttgatgtcca ccagagcatc a                                              21

<210> SEQ ID NO 22
<211> LENGTH: 27
<212> TYPE: DNA
<213> ORGANISM: Mouse
```

```
<400> SEQUENCE: 22
cagcaacttg tggagtatcc tcggacc                                       27

<210> SEQ ID NO 23
<211> LENGTH: 354
<212> TYPE: DNA
<213> ORGANISM: Artificial
<220> FEATURE:
<223> OTHER INFORMATION: Humanized VH region

<400> SEQUENCE: 23
caggtgcagc tggtgcagtc tggggctgag gtgaagaagc ctggggcctc agtgaaggtc    60
tcctgcaagg cttctggata caccttcact aggtactgga taacctgggt gcgccagcgc   120
cccggacaag gacttgagtg gatgggagat atttatcctg gtagtggtag aactaattac   180
aatgagaagt tcaagaacag agtcaccatt accgtggaca catccgcgag cacagcctac   240
atggagctga gcagcctgag atctgaggac acggccgtgt attactgtgc gaattactac   300
ggtagtacct acttctatgt ctgggggcaa gggaccacgg tcaccgtctc ctca         354

<210> SEQ ID NO 24
<211> LENGTH: 336
<212> TYPE: DNA
<213> ORGANISM: Artificial
<220> FEATURE:
<223> OTHER INFORMATION: Humanized VL region

<400> SEQUENCE: 24
gatgttgtga tgacccagtc tccactctcc ctgcccgtca cccttggaca gccggcctcc    60
atctcctgca ggtctagtaa gagtctcctg tataaggacg gaagacata cttgaattgg   120 tttcagcaga ggccagggca gtctccacag ctcctgatct atttgatgtc caccagagca   180
tcaggagtcc cagacaggtt cagtggcagt gggtcaggca ctgatttcac actgaaaatc   240
agcagggtgg aggctgagga tgttggagtt tattactgcc agcaacttgt ggagtatcct   300
cggaccttcg gtggaggcac caaggtggaa atcaaa                            336
```

ANTI-TRANSTHYRETIN HUMANIZED ANTIBODY

TECHNICAL FIELD

The present invention provides an antibody that effectively suppresses formation of amyloid fibril and its deposition to tissues by transthyretin (TTR) as well as a therapeutic method using said antibody. This antibody therapy is based on new therapeutic strategy that normal TTR is not affected but only amyloidogenesis of abnormal TTR is suppressed and is expected to be a novel therapeutic method excellent in safety.

BACKGROUND ART

Amyloidosis is a series of diseases where proteins forming a fiber structure are deposited in the whole-body organs to induce functional disturbance and includes various diseases such as Alzheimer dementia and prion disease (Non-patent reference 1).

Familial Amyloidotic Polyneuropathy (FAP) is autosomal dominant, hereditary, systemic amyloidosis caused by point mutation or deletion of genes of TTR, apolipoprotein A1, gelsolin and the like (Non-patent reference 2). Among these, FAP caused by genetic mutation of TTR is most common. It is known that mutant TTRs form amyloid fibril which is normally deposited in almost all the tissues of the whole body such as the peripheral nerve, the heart, the kidney, the digestive tract, the eye, the brain and the meninges after middle age. It is an intractable disease which shows very bad convalescence of patients and is mortal within around 10 years after onset of disease.

Up till the present, more than 100 point mutations and deletions of TTR gene have been reported. In particular, Val30Met mutation (hereinafter referred to as "V30M"), in which the 30th valine in TTR is mutated to methionine, is most common. There are many patients in Portugal, Sweden and Japan. Since more than 6,000 cases of FAP patients have been confirmed in Portugal, there are not a small number of regions where FAP has not yet been investigated and it is expected that worldwide discovery of FAP patients will continue, it is supposed that there are well over 10,000 patients all over the world. It became known from the recent research that the clinical picture (age of onset, deposit organ specificity, etc.) of FAP is greatly affected by the kind of mutation of TTR gene (Non-patent reference 3). For instance, with regard to age of onset of FAP, L55P mutation shows fulminant clinical picture that the disease develops in one's teens whereas with V122I mutation the disease develops at sixty and thereafter. On the other hand, it is known that V30M mutation shows both types of disease where the disease develops at a younger age and at an older age. With regard to deposit organ specificity, D18G mutation causes deposition at the brain and the meninges to cause central nerves disturbance whereas V30M mutation causes deposition in the whole-body tissues to cause peripheral nerves disturbance and myocardial disturbance (Non-patent references 3 and 4).

TTR is a protein that consists of 127 amino acid residues with a molecular weight of 14 kDa and has a structure that eight β-strands present inside form two antiparallel β-sheets (Non-patent reference 5). TTR is produced predominantly in the liver but also in the ventricular choroid plexus, the retinal pigment epithelium cells of retina, the spleen, and the like. TTR usually forms a stable structure by forming a tetramer with a molecular weight of 55 kDa in blood and functions as a carrier of a vitamin A/retinol-binding protein complex and thyroid hormone T4 mainly in blood and cerebrospinal fluid. Its blood level is as high as 200-400 μg/mL but its half-life is as short as 2 days (Non-patent references 2-6). It is known that in the center of a TTR tetramer are present two homologous T4-binding sites to which T4 binds to stabilize the tetramer structure (Non-patent reference 3). There are various reports about another function of TTR such as the insulin secretion promoting activity, the cerebral nerve protecting activity, and the activity relating to lipid metabolism (Non-patent reference 2). On the other, although a blood level of retinol and thyroid hormone decreases in TTR gene knockout mice, no significant change in phenotypes such as a survival rate and fertility property could be seen (Non-patent reference 7) and thus it remains unknown whether TTR is directly essential for maintenance of actual biological activity.

For amyloidogenesis by TTR, dissociation from a tetramer to a monomer and structural change of a monomer are very important steps (Non-patent reference 3). Among these, it has been revealed that dissociation from a tetramer to a monomer is a rate-determining step of the reaction. On the other hand, in the course where TTR forms amyloid that deposits in the tissues and damages the whole-body organs, a molecular form that exerts toxicity to the tissues has not yet been fully elucidated. It is reported that a monomer and a low molecular weight oligomer such as a dimer exhibit cytotoxicity whereas TTR amyloid of 100 kDa or more dose not (Non-patent reference 5) and so it is to be hoped that future research will clarify relationship between toxicity and a molecular form.

Therapeutic strategy for FAP originating from genetic anomaly of TTR is chiefly classified into the following four groups.
(1) To suppress a produced level of variant TTRs
(2) To stabilize a TTR tetrameric structure containing variant TTRs
(3) To prevent amyloid formation of TTR dissociated from a tetramer
(4) To remove TTR amyloid deposited in tissues Since almost all TTRs in blood are produced in the liver (Non-patent reference 2), the most common therapy at present is liver transplantation as classified in (1) above. Although delay in progression of the disease is observed by liver transplantation, it is inevitable to use an immunosuppressant through life with a great burden to donors and patients. Besides, deposition still continues in several organs including the eyes and the heart and thus exacerbation of symptoms in these organs can be seen in not a few cases (Non-patent reference 8). As such, it is problematic and hence development of an effective therapeutic method is earnestly desired.

For other therapeutic methods than liver transplantation, therapeutic methods using siRNA or an antisense oligonucleotide is at a stage of clinical development in case of the strategy (1). However, with all these methods, production of not only variant TTRs but also wild-type TTR is suppressed and thus their safety assessment when used for a long period of time should carefully be done. As for the strategy (2), a medicament has been developed that binds to the T4-binding sites of a TTR tetramer to thereby stabilize the tetrameric structure. The new medicine Vyndaqul® developed in accordance with the strategy has been approved in EU in 2011 and in Japan in 2013. As the result of clinical test for as long as 30 months, Vyndaqul® exhibited the effect to delay peripheral neuropathy in FAP patients but failed to suppress completely the progress of symptoms (Non-patent reference 9). Also for the strategies (3) and (4), although plural kinds of medicaments are at a stage of clinical development, the status quo is that none of the therapies can be a radical treatment.

PATENT REFERENCES

Patent reference 1: WO 2010030203
Patent reference 2: WO 03004647
Patent reference 3: JP 2010-195710

NON-PATENT REFERENCES

Non-patent reference 1: Glenner, G. G.: Amyloid deposits and amyloidosis: the beta-fibrilloses (second of two parts).: N Engl J Med, 302:1333-1343, 1980
Non-patent reference 2: Ando, Y. & Jono, H.: Pathogenesis and therapy for transthyretin related amyloidosis.: Rinsho Byori, 56:114-120, 2008
Non-patent reference 3: Yoshiki Sekijima: Molecular mechanism of TTR amyloid deposition and its control: Igaku-No-Ayumi, 229:349-356, 2009
Non-patent reference 4: Yuko Motozaki, Shoji Yamada: Molecular epidemiology of familial amyloidotic polyneuropathy (FAP): Igaku-No-Ayumi, 229:357-362, 2009
Non-patent reference 5: Hou, X., Aguilar, M. I. & Small, D. H.: Transthyretin and familial amyloidotic polyneuropathy. Recent progress in understanding the molecular mechanism of neurodegeneration.: FEBS J, 274:1637-1650, 2007
Non-patent reference 6: Araki, S. & Ando, Y.: Transthyretin-related familial amyloidotic polyneuropathy—Progress in Kumamoto, Japan (1967-2012)-.: Proc Jpn Acad Ser B Phys Biol Sci, 86:694-706, 2010
Non-patent reference 7: Episkopou, V., Maeda, S., Nishiguchi, S., Shimada, K., Gaitanaris, G. A., Gottesman, M. E. & Robertson, E. J.: Disruption of the transthyretin gene results in mice with depressed levels of plasma retinol and thyroid hormone.: Proc Natl Acad Sci USA, 90:2375-2379, 1993
Non-patent reference 8: Yukio Ando: Liver transplantation and other treatments for familial amyloidotic polyneuropathy (FAP): Igaku-No-Ayumi, 229:363-368, 2009
Non-patent reference 9: Said, G., Grippon, S. & Kirkpatrick, P.: Tafamidis.: Nat Rev Drug Discov, 11:185-186, 2012
Non-patent reference 10: Goldsteins, G., Persson, H., Andersson, K., Olofsson, A., Dacklin, I., Edvinsson, A., Saraiva, M. J. & Lundgren, E.: Exposure of cryptic epitopes on transthyretin only in amyloid and in amyloidogenic mutants.: Proc Natl Acad Sci USA, 96:3108-3113, 1999
Non-patent reference 11: Terazaki, H., Ando, Y., Fernandes, R., Yamamura, K., Maeda, S. & Saraiva, M. J.: Immunization in familial amyloidotic polyneuropathy: counteracting deposition by immunization with a Y78F TTR mutant.: Lab Invest, 86:23-31, 2006
Non-patent reference 12: Bergstroem, J., Engstroem, U., Yamashita, T., Ando, Y. & Westermark, P.: Surface exposed epitopes and structural heterogeneity of in vivo formed transthyretin amyloid fibrils.: Biochem Biophys Res Commun, 348:532-539, 2006
Non-patent reference 13: Matsubara, K., Mizuguchi, M. & Kawano, K.: Expression of a synthetic gene encoding human transthyretin in *Escherichia coli*.: Protein Expr Purif, 30:55-61, 2003
Non-patent reference 14: Ueda, M., Ando, Y., Hakamata, Y., Nakamura, M., Yamashita, T., Obayashi, K., Himeno, S., Inoue, S., Sato, Y., Kaneko, T., Takamune, N., Misumi, S., Shoji, S., Uchino, M. & Kobayashi, E.: A transgenic rat with the human ATTR V30M: a novel tool for analyses of ATTR metabolisms.: Biochem Biophys Res Commun, 352:299-304, 2007
Non-patent reference 15: Senju, S., Haruta, M., Matsumura, K., Matsunaga, Y., Fukushima, S., Ikeda, T., Takamatsu, K., Irie, A. & Nishimura, Y.: Generation of dendritic cells and macrophages from human induced pluripotent stem cells aiming at cell therapy.: Gene Ther, 18:874-883, 2011.

DISCLOSURE OF THE INVENTION

Technical Problem to be Solved by the Invention

In recent years, FAP treatment by immunotherapy draws attention. It became apparent that, in the course of formation of TTR amyloid, a new epitope (Cryptic Epitope) is exposed on the molecular surface in association with structural change of TTR (Non-patent reference 10).

Under such circumstances, Terazaki et al. immunized human TTR V30M transgenic mice (hTTR Tg mice), a model animal for FAP, with TTR Y78F variant, a variant known as exposing Cryptic Epitope, and assessed its effect on TTR amyloid deposition in mouse tissues (Non-patent reference 11). As a result, the significant increase in an antibody titer of an anti-TTR antibody was confirmed in the group of mice immunized with TTR Y78F variant and, along with this, the decrease in a deposited amount of TTR in the esophagus, the stomach and the intestines could be seen. Likewise, in the similar test with hTTR Tg mice of 18-month old that have already shown TTR deposition, the significant decrease in a deposited amount of TTR could be seen in the Y78F immunization group. These results suggested the possibility that immunization of mice with a TTR variant which exposes Cryptic Epitope induced production of an antibody against TTR in the body of mice and as a consequence TTR amyloid deposition was suppressed.

On the other hand, Bergstroem et al. immunized rabbits with a TTR 115-124 peptide, which is one of Cryptic Epitope, to prepare an anti-TTR115-124 polyclonal antibody (Non-patent reference 12). This polyclonal antibody was administered to hTTR V30M transgenic rats to assess the effect on TTR deposition in rat tissues. As a result, it was found that a deposited amount of TTR in the intestinal tracts of rat significantly decreased in the group with administration of the polyclonal antibody (Patent reference 3).

From these results, there may be the possibility that an antibody specifically recognizing Cryptic Epitope of TTR specifically binds to TTR amyloid (or TTR with structural change that constitutes TTR amyloid) to thereby promote inhibition of formation or removal of TTR amyloid. Namely, the possibility is suggested that an antibody specifically recognizing Cryptic Epitope of TTR can be a novel therapeutic agent of FAP.

Research of an anti-TTR antibody based on this concept was reported by BIOCODEX. BIOCODEX prepared mouse monoclonal antibody AD7F6, which is specific to amyloidogenetic TTR, using TTR knockout mice and showed that the monoclonal antibody suppressed tissue deposition of TTR using Tg mice (ATTR V30M), a disease model of FAP (Patent reference 1). The patent of BIOCODEX claims an amino acid sequence of the mouse antibody and thus it is difficult to administer the antibody to humans. It is not clearly described as to the reactivity of this antibody with V30M variant having a tetrameric structure. In FAP patients having V30M mutation, V30M variant in blood having a tetrameric structure is thought to be dissociated to monomers, a portion of which causes structural change to form amyloid. It is thus the requisites for realizing a more effective and safer antibody therapy to be an antibody that does not react with V30M variant having a tetrameric structure but reacts only with such V30M variant that formed amyloid (or that is in the midst of amyloidogenesis). With regard to the reactivity of this antibody, since only serum of V30M carriers is used as a clinical sample, its reactivity with tissue-depositing amyloid in the body of patients is unknown.

Research of an anti-TTR antibody based on the same concept was reported by the group of Porto University in Portugal (Non-patent reference 10). It reported that mouse monoclonal antibodies mAb 39-44 and mAb 56-61 were prepared which were specific to TTR with structural change and that these antibodies reacted with amyloid of V30M variant derived from the living body. It is stated clearly, however, that these antibodies did not show an inhibitory activity to amyloidogenesis and only the possibility of their use for FAP diagnosis is referred to.

As described above, although polyclonal antibodies or monoclonal antibodies obtained by immunization of mice (or rats) with Cryptic Epitope of TTR were reported to suppress TTR deposition, an antibody having the activity to specifically bind to TTR with structural change or the activity to inhibit TTR-fibrillization and a humanized antibody or a human antibody suitable for administration to humans were not reported.

Means for Solving the Problems

The present inventors recognized that in TTR amyloidosis a portion of tetrameric TTRs is dissociated into monomeric TTRs which undergo structural change to form amyloid but on the other hand there remain tetrameric TTRs which function normally. Thus, the present inventors have investigated an antibody that specifically binds to TTRs with structural change and has the activity to inhibit TTR-fibrillization. Aiming at achieving antibody therapy to TTR amyloidosis as a final goal, the present inventors have diligently investigated a humanized antibody having the above activity to complete the present invention.

Namely, the present invention relates to the followings:
(1) A humanized antibody having the activity to inhibit fibrillization of transthyretin (TTR);
(2) The humanized antibody of (1) which specifically recognizes TTRs with structural change;
(3) The humanized antibody of (1) or (2) which specifically binds to TTR amyloid;
(4) The humanized antibody of any one of (1) to (3) which binds to TTR amyloid derived from two or more kinds of variant TTRs;
(5) The humanized antibody of (4) wherein the variant TTR is TTR having a mutation selected from the group consisting of D18G, V30M, E54K, L55P, Y114C, Y116S and V122I;
(6) The humanized antibody of any one of (1) to (5) which promotes removal of TTR amyloid;
(7) The humanized antibody of any one of (1) to (6) which promotes the phagocytic ability of macrophages to TTR amyloid;
(8) The humanized antibody of any one of (1) to (7) wherein an epitope is a sequence comprising position 118 to position 122 of TTR;
(9) The humanized antibody of (8) wherein an epitope is position 118 to position 122 of TTR;
(10) The humanized antibody of any one of (1) to (9) which has a therapeutic effect and/or a preventive effect to TTR amyloidosis;
(11) The humanized antibody of (10) wherein the TTR amyloidosis is Familial Amyloidotic Polyneuropathy FAP;
(12) The humanized antibody of (10) wherein the TTR amyloidosis is Senile Systemic Amyloidosis (SSA);
(13) The humanized antibody of any one of (1) to (12) which comprises a complementarity determining region of an H chain consisting of the polypeptide of (a) or (b) below and a complementarity determining region of an L chain consisting of the polypeptide of (c) or (d) below:
  (a) a polypeptide consisting of the amino acid sequence as shown in SEQ ID NOs: 1 to 3;
  (b) a polypeptide which consists of the amino acid sequence as shown in SEQ ID NOs: 1 to 3 wherein one or several amino acid residue(s) is/are substituted, deleted, inserted and/or added and which can be a complementarity determining region of an H chain to TTR;
  (c) a polypeptide consisting of the amino acid sequence as shown in SEQ ID NOs: 4 to 6;
  (d) a polypeptide which consists of the amino acid sequence as shown in SEQ ID NOs: 4 to 6 wherein one or several amino acid residue(s) is/are substituted, deleted, inserted and/or added and which can be a complementarity determining region of an L chain to TTR;
(14) The humanized antibody of any one of (1) to (13) which comprises a complementarity determining region of an H chain consisting of the polypeptide of (e) or (f) below and a complementarity determining region of an L chain consisting of the polypeptide of (g) or (h) below:
  (e) a polypeptide consisting of the amino acid sequence as shown in SEQ ID NO: 7;
  (f) a polypeptide which consists of the amino acid sequence as shown in SEQ ID NO: 7 wherein one or several amino acid residue(s) is/are substituted, deleted, inserted and/or added and which can be a complementarity determining region of an H chain to TTR;
  (g) a polypeptide consisting of the amino acid sequence as shown in SEQ ID NO: 8;
  (h) a polypeptide which consists of the amino acid sequence as shown in SEQ ID NO: 8 wherein one or several amino acid residue(s) is/are substituted, deleted, inserted and/or added and which can be a complementarity determining region of an L chain to TTR;
(15) An H chain variable region fragment comprising a complementarity determining region of an H chain consisting of the polypeptide of (a) or (b) below:
  (a) a polypeptide consisting of the amino acid sequence as shown in SEQ ID NOs: 1 to 3;
  (b) a polypeptide which consists of the amino acid sequence as shown in SEQ ID NOs: 1 to 3 wherein one or several amino acid residue(s) is/are substituted, deleted, inserted and/or added and which can be a complementarity determining region of an H chain to TTR;
(16) An L chain variable region fragment comprising a complementarity determining region of an L chain consisting of the polypeptide of (c) or (d) below:

(c) a polypeptide consisting of the amino acid sequence as shown in SEQ ID NOs: 4 to 6;

(d) a polypeptide which consists of the amino acid sequence as shown in SEQ ID NOs: 4 to 6 wherein one or several amino acid residue(s) is/are substituted, deleted, inserted and/or added and which can be a complementarity determining region of an L chain to TTR;

(17) An H chain variable region fragment comprising a complementarity determining region of an H chain consisting of the polypeptide of (e) or (f) below:

(e) a polypeptide consisting of the amino acid sequence as shown in SEQ ID NO: 7;

(f) a polypeptide which consists of the amino acid sequence as shown in SEQ ID NO: 7 wherein one or several amino acid residue(s) is/are substituted, deleted, inserted and/or added and which can be a complementarity determining region of an H chain to TTR;

(18) An L chain variable region fragment comprising a complementarity determining region of an L chain consisting of the polypeptide of (g) or (h) below:

(g) a polypeptide consisting of the amino acid sequence as shown in SEQ ID NO: 8;

(h) a polypeptide which consists of the amino acid sequence as shown in SEQ ID NO: 8 wherein one or several amino acid residue(s) is/are substituted, deleted, inserted and/or added and which can be a complementarity determining region of an L chain to TTR;

(19) A single-chain variable region fragment of an antibody to TTR, which is formed by linking the H chain variable region fragment comprising a complementarity determining region of an H chain of (15) or the H chain variable region fragment of (17) and the L chain variable region fragment comprising a complementarity determining region of an L chain of (16) or the L chain variable region fragment of (18);

(20) The humanized antibody of any one of (1) to (12) or a fragment thereof, which is formed by linking a human-derived constant region to the H chain variable region fragment comprising a complementarity determining region of an H chain of (15) or the H chain variable region fragment of (17) and/or to the L chain variable region fragment comprising a complementarity determining region of an L chain of (16) or the L chain variable region fragment of (18);

(21) A gene coding for the antibody or a fragment thereof of any one of (1) to (20);

(22) A recombinant expression vector comprising the gene of (21);

(23) A transformant wherein the gene of (21) or the expression vector of (22) is introduced;

(24) An apparatus for detecting TTR amyloid comprising the antibody or a fragment thereof of any one of (1) to (20);

(25) A carrier for removing TTR amyloid comprising the antibody or a fragment thereof of any one of (1) to (20);

(26) A reagent for detecting TTR amyloid comprising the antibody or a fragment thereof of any one of (1) to (20);

(27) A diagnostic agent for TTR amyloidosis comprising the antibody or a fragment thereof of any one of (1) to (20);

(28) The diagnostic agent of (27) wherein the TTR amyloidosis is Familial Amyloidotic Polyneuropathy (FAP);

(29) The diagnostic agent of (27) wherein the TTR amyloidosis is Senile Systemic Amyloidosis (SSA);

(30) A TTR-fibrillization inhibitor comprising the antibody or a fragment thereof of any one of (1) to (20);

(31) A pharmaceutical composition for the prevention and/or the treatment of TTR amyloidosis comprising the antibody or a fragment thereof of any one of (1) to (20);

(32) The pharmaceutical composition of (31) wherein the TTR amyloidosis is Familial Amyloidotic Polyneuropathy (FAP);

(33) The pharmaceutical composition of (31) wherein the TTR amyloidosis is Senile Systemic Amyloidosis (SSA).

Effects of the Invention

The present inventors have created a monoclonal antibody that specifically recognizes TTRs with structural change and succeeded in opening up a path to development of an antibody drug that enables the treatment of FAP. The antibody of the present invention effectively suppresses formation of amyloid fibril and its deposition to tissues by TTR but does not react with normal TTR functioning in blood. Thus, the antibody of the present invention is expected to be an antibody drug excellent in safety. Besides, as an action mechanism, two distinct effects can be expected: (1) formation of amyloid fibril and its deposition to tissues by TTR are suppressed; and (2) TTR amyloid deposited to tissues is also affected to accelerate its clearance, i.e. accumulated amyloid is decreased. These effects can never be attained by the prior art or previous development articles. Therefore, the antibody therapy of the present invention is greatly expected as a novel therapeutic strategy to TTR amyloidosis.

As described above, the antibody of the present invention is not only expected to provide a novel therapeutic method other than liver transplantation to FAP but also has the possibility for use as a therapeutic agent for Senile Systemic Amyloidosis (SSA). For TTR amyloidosis, not only FAP caused by genetic mutation of TTR but also SSA caused by amyloid deposition formed by wild-type TTR chiefly at the heart are known. It is regarded as Alzheimer disease in the heart. Amyloid deposition is also seen in the lung, the vascular wall, the renal medulla and the like. Patients often complain no symptom or symptoms in the heart (indolent heart failure) and sometimes carpal tunnel syndrome. The onset of the disease is observed from the 60's onward and it is said that the onset is observed in approximately one in four people of 80's. In the U.S. alone, an estimated number of more than 400,000 patients is reported. No effective therapeutic method for this disease has been established. The antibody of the present invention, as having the activity to inhibit fibrillization of wild-type TTR, is expected to be applied to SSA.

The antibody product of the present invention is expected to be applied not only to FAP but also to amyloidogenetic diseases in various organs caused by TTR and thus is expected to make a contribution to therapy of patients of these many diseases where a therapeutic method has not yet been found up till the present.

BEST MODE FOR CARRYING OUT THE INVENTION

Figure 1:
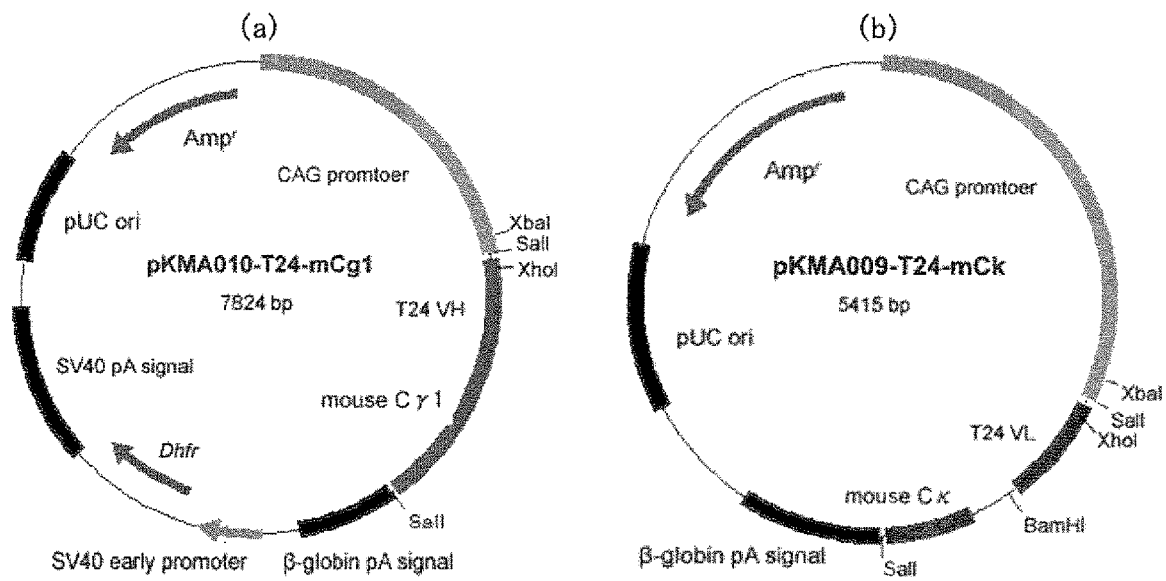
FIG. 1 shows maps of (a) mouse T24 antibody H chain expression vector pKMA010-T24-mCg1, and (b) mouse T24 antibody L chain expression vector pKMA009-T24-mCk.

The specific embodiments of the present invention are explained hereinbelow. The present invention is not construed to be limited to these embodiments.

1. Antibody of the Present Invention and a Fragment Thereof

In accordance with the present invention, focusing on the fact that the amino acid residues at positions 115-124 of TTR are not presented on the surface in case of normal (tetramer) TTR but are exposed on the surface when TTR is fibrillized, TTR115-124 was selected as an antigen for preparing an antibody. After TTR knockout mouse was immunized with said antigen, a mouse antibody was prepared and an amino acid sequence of the mouse antibody was humanized to prepare a humanized antibody.

TTR115-124 may be prepared by chemical synthesis or alternatively by purifying expression product from $E.$ $coli$ and the like. In the latter case, a nucleotide sequence corresponding to 115-124 is amplified with a primer DNA designed to amplify said nucleotide sequence using the nucleotide sequence of human TTR as a template. Said nucleotide sequence is then incorporated into an expression vector and the expression vector is introduced into a host ($E.$ $coli$ and the like). Using the host, TTR115-124 is expressed and then purified for use as an antigen. TTR115-124, obtained by chemical synthesis or expression procedure, may be bound to a carrier protein (KLH, BSA and the like) and then used for immunization of mice. A method for binding to a carrier protein includes the use of Immunogen EDC Kit with mcKLH and BSA (Thermo). One molecule or two molecules of TTR115-124 may be bound to a carrier protein. TTR115-124 may be bound to a carrier protein at any site of the N terminal, the C terminal, or within the molecule.

Next, a method for preparing a mouse antibody is exemplified below. TTR knockout mouse is immunized with TTR115-124. TTR knockout mouse may be prepared by the method described in Non-patent reference 7. A frequency of immunization with TTR115-124 is preferably twice or more and each immunization is done preferably at intervals of around three weeks. A frequency of immunization and intervals may suitably be changed while observing an extent of increase in antibody titer to TTR. Then, antibody-producing cells are collected from the mouse spleen and, in accordance with the conventional hybridoma technique, fused with myeloma cells to prepare hybridomas. The hybridomas are subject to limiting dilution and then cultured to collect culture supernatant. Mouse antibodies contained in the culture supernatant are purified and tested for the reactivity with TTR115-124 by ELISA test. As an example of ELISA test, TTR115-124 is directly or indirectly immobilized to ELISA plate. TTR115-124 may be immobilized to a plate at any of the N terminal and the C terminal of TTR115-124. The mouse antibodies are then added to the plate for reaction. Then, an enzyme-labeled anti-mouse antibody and a substrate are added in this order to the plate and the substrate is detected. With such ELISA test as an index, an antibody to TTR115-124 is selected.

Next, a step for selecting an antibody that specifically binds to TTR amyloid may be provided. A method for testing the binding to TTR amyloid is exemplified below. TTR peptide is left to stand under acidic conditions for a sufficient period of time for fibrillization to form TTR amyloid. The acidic conditions and the period of time for fibrillization may suitably be changed depending on the kind of TTR peptide. Existence or nonexistence of TTR fibrillization can be confirmed by thioflavin T assay. The acidic conditions are preferably pH 5.0 or less, more preferably pH 3.0 to pH 4.0. The period of time for fibrillization is preferably overnight. Acid-treated TTR (TTR amyloid) or non-treated TTR (normal TTR) are bound to ELISA plate and then reacted with a mouse antibody. An antibody that binds to TTR amyloid at a higher binding capacity than normal TTR may be selected.

Next, a method for preparing a humanized antibody from a mouse antibody is exemplified below. After mRNAs are collected from hybridomas producing a mouse antibody, reverse transcription is performed to prepare cDNAs. Using cDNAs as a template, a VH region and a VL region are amplified. After these regions are introduced into a suitable plasmid, nucleotide sequences of the VH region or the VL region are analyzed. In the VH region or the VL region, portions corresponding to CDR (CDRs 1-3) are specified. Next, in order to graft amino acid sequences of CDRs of a mouse antibody into amino acid sequences of the VH region or the VL region of a human antibody, a human antibody suitable for CDR graft is selected. Amino acid sequences are designed where amino acid sequences of CDRs 1-3 of a mouse antibody are inserted into amino acid sequences of the VH region or the VL region of a human antibody. Said amino acid sequences are converted to nucleotide sequences. Said nucleotide sequences are chemically synthesized and inserted into an expression vector containing nucleotide sequences coding for constant regions of H chain or L chain. Said expression vector is introduced into a suitable host (an animal cell) and, using the host, a humanized antibody is expressed.

In accordance with the present invention, modified amino acid sequences were designed where amino acid sequences of framework regions of the VH region or the VL region of said humanized antibody were modified and, based on the modified amino acid sequences, nucleotide sequences were chemically synthesized. With the same procedures as above, a modified humanized antibody was prepared.

A method for analyzing an epitope for the mouse antibody and the humanized antibody as above (hereinafter collectively referred to as "antibody") is exemplified below. Modified human TTRs are prepared where one amino acid residue in positions 115-124 of the amino acid sequence of human TTR is altered. Conventional site-directed mutagenesis is used to prepare genes of the modified TTRs. The genes are inserted into an expression vector and then expressed and purified with a suitable host (preferably $E.$ $coli$). Such modified TTRs include Y114C, S115A, Y116A, S117A, T118A, T119A, A120S, V121A, V122A, V122I, T123A and N124A. With conventional Western blotting, the modified TTRs are electrophoresed on SDS-PAGE and are reacted with an antibody of the analysis object to detect reactivity between the variants and the antibody. When modified TTRs with reduced binding to the antibody are found, the modified portion may be considered to be an epitope. The antibody of the present invention had an epitope at positions 118-122.

The mouse antibody and humanized antibody as above may be subject to tests for the specific reactivity to TTRs with structural change, the reactivity with fibrillized TTR, immunostaining to tissues derived from TTR patients, the inhibitory activity to fibrillization by variant TTR, the promoting activity to the macrophage phagocytic ability to TTR amyloid, and the drug efficacy evaluation using FAP animal model.

A method for analyzing specific reactivity to TTRs with structural change includes a method using surface plasmon resonance. Wild-type TTR tetramer, variant TTR (V30M etc.) tetramer, or variant TTR amyloid are prepared. A method for preparing wild-type TTR tetramer and variant TTR tetramer includes a method of Matsubara et al. (Non-patent reference 13). A method for preparing variant TTR amyloid includes the process in which the above tetrameric TTR peptide, after adjusted at 3 mg/mL, is mixed with a solution of an equivalent amount of 200 mM acetate buffer and 100 mM NaCl for reaction at 37° C. for 16 hours. For TTRs after the reaction, fibrillization may be confirmed by measuring fluorescence intensity by ThioflavinT assay (excitation wavelength 440 nm, fluorescent wavelength 480 nm).

Next, these preparations are let to bind to sensor chips, to which an antibody of the analysis object is added for reaction with the sensor chips, thereby indicating the binding of TTR with the antibody as response unit (RU). Here, those antibodies that have RU for variant TTR amyloid significantly higher than RU for wild-type TTR tetramer and variant TTR tetramer are thought to specifically recognize TTRs with structural change. As compared to such tetrameric TTRs, an antibody that specifically recognizes TTRs with a bigger size of molecular structure than tetramer (e.g. TTR amyloid) may also be regarded as an antibody that specifically recognizes TTRs with structural change.

A method for analyzing the activity to inhibit fibrillization of variant TTR is exemplified below. A solution containing TTR and an antibody to be evaluated is mixed with a surfactant at a final concentration of 0.01-1% and left to stand at such a temperature for such a period of time that allows for TTR to form fibril. Fluorescence intensity is measured by ThioflavinT assay (excitation wavelength 440 nm, fluorescent wavelength 480 nm) to evaluate a degree of TTR-fibrillization. A surfactant includes benzalkonium chloride, sodium deoxycholate, Zwittergent3-16 and NP-40. Most preferable is deoxycholate. A final concentration includes 0.01-1%, and is most preferably 0.1%. Time and temperature includes at 37° C. for 3 to 4 days but may suitably be arranged for their combination. This method of analysis is an excellent evaluation system where denaturation of an antibody to be evaluated may be prohibited since the analysis can be performed at pH close to neutrality.

A method for analyzing the macrophage phagocytic ability to TTR amyloid is exemplified below. Human iPS cells are prepared from skin tissue from healthy adults by the conventional method and are further differentiated to macrophages by the conventional method. TTR fibril and $5 \times 10^4$ cells of the differentiated macrophages are mixed together. An antibody to be evaluated is added and the mixture is cultured for a fixed period of time (e.g. 3 days). A residual quantity of TTR after culture is measured by ELISA to evaluate the phagocytic ability of macrophage.

A method for analyzing the reactivity between the antibody of the present invention and TTR amyloid is exemplified below. Wild-type TTR and variant TTR are treated under acidic conditions for a period of time sufficient for TTR-fibrillization to prepare TTR fibril. Time for fibrillization may suitably be selected depending on pH or the kinds of TTR. The samples after the acid treatment are electrophoresed on Native PAGE and subject to silver staining. A broad band at a higher position than 60 kDa may be an index for TTR-fibrillization. Using the conventional Western blotting, the TTR amyloid is electrophoresed on SDS-PAGE and antibodies of analysis object are reacted thereto for detection. An antibody that has a higher reactivity with TTR amyloid as compared to TTR with no acid treatment (TTR not undergo fibrillization) may be regarded as an antibody having the binding activity to TTR amyloid.

A method for the drug efficacy evaluation using FAP animal model is exemplified below. Using V30M Tg rat (Non-patent reference 13; transgenic rat where a gene of human TTR with mutation of valine at position 30 to methionine in the amino acid sequence of TTR is introduced), a fixed amount (e.g. 10 mg/kg) of an antibody to be evaluated is administered for a fixed period of time (e.g. for 6 months) at a fixed frequency (e.g. once per week). After administration, the large intestine is taken out by autopsy and formalin fixed. The fixed tissue of the large intestine is embedded in a paraffin block to prepare tissue section. The tissue section is subject to immunostaining using Polyclonal Rabbit Anti-Human Prealbumin (Dako), HRP-labelled Goat anti-Rabbit IgG (Dako) and a degree of TTR deposition in the muscular layer of the large intestine is digitized and compared between the groups.

The humanized antibody of the present invention has the inhibitory activity to TTR-fibrillization, the specific binding activity to TTRs with structural change, the effect of promoting the phagocytic ability of macrophage to TTR amyloid, the binding activity to TTR amyloid, and the effect to FAP animal model. As a result of analysis of an epitope for the antibody of the present invention, it was present at TTR118-122. Thus, the present invention includes the humanized antibodies as follows:

(1) An antibody having the activity to inhibit fibrillization of TTR;

(2) An antibody which specifically recognizes TTRs with structural change and does not recognize tetrameric functional TTR;

(3) An antibody which specifically binds to TTR amyloid;

(4) An antibody which promotes removal of TTR amyloid;

(5) An antibody which promotes the phagocytic ability of macrophages to TTR amyloid;

(6) An antibody which has a therapeutic effect and/or a preventive effect to TTR amyloidosis;

(7) A humanized antibody which has an epitope of TTR118-122.

The antibodies of (1) to (7) above may have one characteristic feature as shown in each of (1) to (7) or may have a combination of characteristic features as shown in (1) to (7).

For the humanized antibody of the present invention, the amino acid and nucleotide sequences of CDRs 1-3 of VH region or VL region are shown in the following table.

TABLE 1

| | | | |
|---|---|---|---|
| VH region | CDR1 | RYWIT | SEQ ID NO: 1 |
| | | aggtactggataacc | SEQ ID NO: 17 |
| | CDR2 | DIYPGSGRTNYNEKFKN | SEQ ID NO: 2 |
| | | gatatttatcctggtagtggtagaact aattacaatgagaagttcaagaac | SEQ ID NO: 18 |
| | CDR3 | YYGSTYFYV | SEQ ID NO: 3 |
| | | tactacggtagtacctacttctatgtc | SEQ ID NO: 19 |
| VL region | CDR1 | RSSKSLLYKDGKTYLN | SEQ ID NO: 4 |
| | | aggtctagtaagagtctcctgtataag gacgggaagacatacttgaat | SEQ ID NO: 20 |
| | CDR2 | LMSTRAS | SEQ ID NO: 5 |
| | | ttgatgtccaccagagcatca | SEQ ID NO: 21 |
| | CDR3 | QQLVEYPRT | SEQ ID NO: 6 |
| | | cagcaacttgtggagtatcctcggacc | SEQ ID NO: 22 |

Thus, the present invention includes the humanized antibody having the following characteristic features of the amino acid sequence:

(8) A humanized antibody which comprises a complementarity determining region of an H chain consisting of the polypeptide of (a) or (b) below and a complementarity determining region of an L chain consisting of the polypeptide of (c) or (d) below:
   (a) a polypeptide consisting of the amino acid sequence as shown in SEQ ID NOs: 1 to 3;
   (b) a polypeptide which consists of the amino acid sequence as shown in SEQ ID NOs: 1 to 3 wherein one or several amino acid residue(s) is/are substituted, deleted, inserted and/or added and which can be a complementarity determining region of an H chain to TTR;
   (c) a polypeptide consisting of the amino acid sequence as shown in SEQ ID NOs: 4 to 6;
   (d) a polypeptide which consists of the amino acid sequence as shown in SEQ ID NOs: 4 to 6 wherein one or several amino acid residue(s) is/are substituted, deleted, inserted and/or added and which can be a complementarity determining region of an L chain to TTR.

The above humanized antibody may also have characteristic features as shown in each of (1) to (7).

In accordance with the present invention, plural kinds of humanized antibodies were prepared where amino acid sequences in framework regions of the VH region or the VL region were modified. By way of example, such humanized antibodies include the VH region or the VL region encoded by the following amino acid and nucleotide sequences.

TABLE 2

| | | |
|---|---|---|
| VH region | QVQLVQSGAEVKKPGASVKVSCKASGYTETRYWITW VRQRPGQGLEWMGDIYPGSGRTNYNEKEKNRVTITV DTSASTAYMELSSLRSEDTAVYYCANYYGSTYFYVW GQGTTVTVSS | SEQ ID NO: 7 |
| | caggtgcagctggtgcagtctggggctgaggtgaag aagcctggggcctcagtgaaggtctcctgcaaggct tctggatacacctt cactggtactggataacctgg gtgcgccagcgcccc ggacaaggacttgagtggatg ggagatatttatcctggtagtggtagaactaattac aatgagaattcaagaacagagtcaccattaccgtgg acacatccgcgagcacagcctacatggagctgagca gcctgagatctgaggacacggccgtgtattactgtg cgaattactacggtagtacctacttctatgtctggg ggcaagggaccacggtcaccgtctcctca | SEQ ID NO: 23 |
| VL region | DVVMTQSPLSLPVTLGQPASISCRSSKSLLYKDGKT YLNWFQQRPGQSPQLLIYLMSTRASGVPDRFSGSGS GTDFTLKISRVEAEDVGVYYCQQLVEYPRTFGGGTK VEIK | SEQ ID NO: 8 |

TABLE 2-continued

| | |
|---|---|
| gatgttgtgatgacccagtctccactctccctgccc gtcacccttggacagccggcctccatctcctgcagg tctagtaagagtctcctgtataaggacgggaagaca tacttgaattggtttcagcagaggccagggcagtct ccacagctcctgatctatttgatgtccaccagagca tcaggagtcccagacaggttcagtggcagtgggtca ggcactgatttcacactgaaaatcagcagggtggag gctgaggatgttggagtttattactgccagcaactt gtggagtatcctcggaccttcggtggaggcaccaag gtggaaatcaaa | SEQ ID NO: 24 |

Thus, the present invention includes the following humanized antibody:
(9) A humanized antibody which comprises a complementarity determining region of an H chain consisting of the polypeptide of (e) or (f) below and a complementarity determining region of an L chain consisting of the polypeptide of (g) or (h) below:
   (e) a polypeptide consisting of the amino acid sequence as shown in SEQ ID NO: 7;
   (f) a polypeptide which consists of the amino acid sequence as shown in SEQ ID NO: 7 wherein one or several amino acid residue(s) is/are substituted, deleted, inserted and/or added and which can be a complementarity determining region of an H chain to TTR;
   (g) a polypeptide consisting of the amino acid sequence as shown in SEQ ID NO: 8;
   (h) a polypeptide which consists of the amino acid sequence as shown in SEQ ID NO: 8 wherein one or several amino acid residue(s) is/are substituted, deleted, inserted and/or added and which can be a complementarity determining region of an L chain to TTR.

The above humanized antibody may also have characteristic features as shown in each of (1) to (8).

The present invention includes the H chain variable region fragment comprising the following CDR of H chain:
(10) An H chain variable region fragment comprising a complementarity determining region of an H chain consisting of the polypeptide of (a) or (b) below:
   (a) a polypeptide consisting of the amino acid sequence as shown in SEQ ID NOs: 1 to 3;
   (b) a polypeptide which consists of the amino acid sequence as shown in SEQ ID NOs: 1 to 3 wherein one or several amino acid residue(s) is/are substituted, deleted, inserted and/or added and which can be a complementarity determining region of an H chain to TTR.

The present invention includes the L chain variable region fragment comprising the following CDR of L chain:

(11) An L chain variable region fragment comprising a complementarity determining region of an L chain consisting of the polypeptide of (c) or (d) below:
  (c) a polypeptide consisting of the amino acid sequence as shown in SEQ ID NOs: 4 to 6;
  (d) a polypeptide which consists of the amino acid sequence as shown in SEQ ID NOs: 4 to 6 wherein one or several amino acid residue(s) is/are substituted, deleted, inserted and/or added and which can be a complementarity determining region of an L chain to TTR.

The present invention includes the following H chain variable region fragment:

(12) An H chain variable region fragment consisting of the polypeptide of (e) or (f) below:
  (e) a polypeptide consisting of the amino acid sequence as shown in SEQ ID NO: 7;
  (f) a polypeptide which consists of the amino acid sequence as shown in SEQ ID NO: 7 wherein one or several amino acid residue(s) is/are substituted, deleted, inserted and/or added and which can be a complementarity determining region of an H chain to TTR.

The present invention includes the following L chain variable region fragment:

(13) An L chain variable region fragment consisting of the polypeptide of (g) or (h) below:
  (g) a polypeptide consisting of the amino acid sequence as shown in SEQ ID NO: 8;
  (h) a polypeptide which consists of the amino acid sequence as shown in SEQ ID NO: 8 wherein one or several amino acid residue(s) is/are substituted, deleted, inserted and/or added and which can be a complementarity determining region of an L chain to TTR.

The present invention includes the following single-chain variable region fragment:

(14) A single-chain variable region fragment of an antibody to TTR, which is formed by linking the H chain variable region fragment comprising a complementarity determining region of an H chain of (10) or the H chain variable region fragment of (12) and the L chain variable region fragment comprising a complementarity determining region of an L chain of (11) or the L chain variable region fragment of (13).

For a single-chain variable region fragment, an H chain variable region fragment and an L chain variable region fragment are usually linked to each other via a suitable peptide linker and the like. For the peptide linker, any single-chain peptide consisting of e.g. 10 to 25 amino acid residues is used.

The present invention includes the following antibody or a fragment thereof, which is formed by linking a human-derived constant region to the H chain variable region fragment and/or to the L chain variable region fragment:

(15) A human-derived antibody to TTR or a fragment thereof, which is formed by linking a human-derived constant region to the H chain variable region fragment comprising a complementarity determining region of an H chain of (10) or the H chain variable region fragment of (12) and/or to the L chain variable region fragment comprising a complementarity determining region of an L chain of (11) or the L chain variable region fragment of (13).

The above antibody or a fragment thereof where a human-derived constant region is bound may be Fab, Fab', F(ab')$_2$, scAb having at least a portion of Fc region, or scFvFc, or even a complete antibody. As used herein, scAb is that which is formed by linking a portion of domain (c domain) of L chain or H chain constant region to scFv whereas scFvFc is that which is formed by linking a portion of constant region of H chain (Fc region) to scFv.

The antibody as mentioned above also includes a protein structurally relevant to an antibody and refers to an immunoglobulin. Besides, the antibody of the present invention may be of any class of IgA, IgD, IgE, IgG or IgM. In other words, the antibody of the present invention may be a monomer or a polymer such as a dimer, a trimer, a tetramer or a pentamer.

As used herein, the phrase "wherein one or several amino acid residue(s) is/are substituted, deleted, inserted and/or added" means that such a number of amino acid residue(s) that can afford to substitution, deletion, insertion and/or addition is/are substituted, deleted, inserted and/or added by a known method for preparing a mutant protein such as site-directed mutagenesis. Thus, for instance, the above polypeptide (b) is a mutant peptide of the above polypeptide (a). As used herein, the term "mutation" means principally mutation artificially introduced by a known method for preparing a mutant protein but may also be the similar mutant protein which is present in nature (e.g. human) and isolated and purified.

The "mutation", when the antibody of the present invention or a fragment thereof is used as a pharmaceutical composition (i.e. administered to human), is done within such a range that a human-derived structure or human does not induce immune reaction and, when the antibody of the present invention or a fragment thereof is used as a detection device or a diagnostic agent (i.e. not administered to human), is not particularly limited. Besides, when the antibody of the present invention or a fragment thereof is administered to human, mutation is performed preferably within such a range that a higher order structure of CDR recognizing an antigen is maintained.

The antibody of the present invention or a fragment thereof may comprise an additional polypeptide. Such addition of a polypeptide includes epitope labelling of the protein of the present invention with e.g. His, Myc, Flag, etc.

Besides, the antibody of the present invention or a fragment thereof may be bound with a modifier so as to improve its stability or antibody titer. Namely, the antibody of the present invention or a fragment thereof may be a modified antibody. A modifier includes, for instance, a sugar chain, a macromolecule, and the like. When modification is performed with a sugar chain, the sugar chain may possibly have a certain physiological activity. However, when modification is performed with a simple macromolecule such as polyethylene glycol (PEG), the molecule per se does not show a physiological activity. Besides, it is possible that PEGylation suppresses absorption in the liver or improve stability in blood. Thus, a modifier is preferably a simple macromolecule such as PEG.

As is the case with the preparation of a mutant peptide, modification of the antibody of the present invention or a fragment thereof with a modifier, when the antibody of the present invention or a fragment thereof is used as a therapeutic agent, is done within such a range that human does not induce immune reaction and, when the antibody of the present invention or a fragment thereof is used as a detection device or a diagnostic agent, is not particularly limited. Besides, when the antibody of the present invention or a fragment thereof is administered to human, modification is performed preferably within such a range that a higher order structure of CDR recognizing an antigen is maintained.

2. Gene of the Present Invention

The present invention includes a gene coding for the antibody or a fragment thereof of the above item 1. For instance, the present invention includes a gene including the following nucleotide sequences as an open reading frame (ORF) region and a modified gene with these nucleotide sequences partially modified:

(1) nucleotide sequence comprising SEQ ID NOs:1-3 and/or SEQ ID NOs:4-6;
(2) nucleotide sequence comprising SEQ ID NO:7 and/or SEQ ID NO:8.

The above gene, coding for the antibody of the present invention or a fragment thereof, may be introduced into a suitable host (e.g. bacteria, yeast) for expression of the antibody of the present invention or a fragment thereof.

Besides, the above gene may be one further comprising an untranslated region (UTR) or a sequence of a vector (including a sequence of an expression vector) in addition to a nucleotide sequence coding for the antibody or a fragment thereof of the above item 1. For instance, the sequence of SEQ ID NO: 13 or 14 is linked to a sequence of a vector to form the gene of the present invention. The resultant gene may then be amplified in a suitable host to amplify the gene of the present invention as desired. Also, a portion of the gene of the present invention may be used as a probe.

The gene of the present invention may be utilized as a gene therapy agent in the diseases associated with TTR amyloid. The gene therapy agent may be designed to express the antibody of the present invention or a fragment thereof within the living body after administration thereof so that the antibody of the present invention or a fragment thereof is formed within the living body after ingestion thereof to thereby exhibit the similar effect to that of the above inhibitor.

3. Recombinant Expression Vector of the Present Invention

The present invention includes a recombinant expression vector comprising the gene of the above item 2, i.e. the gene coding for the antibody or a fragment thereof of the above item 1. For instance, the recombinant expression vector of the present invention includes the one where cDNA having the nucleotide sequence of SEQ ID NO: 7 or 8 is inserted. The recombinant expression vector may be prepared with, but not particularly limited to, plasmid, phage, cosmid and the like.

A concrete sort of a vector is not particularly limited but such a vector that allows for expression in a host cell may suitably be selected. Namely, a promoter sequence may suitably be selected so as to ensure gene expression depending on the kind of a host cell and a variety of plasmids etc. into which the promoter and the gene of the present invention are inserted may be used as an expression vector.

A variety of markers may be used for confirming if the gene of the present invention is introduced into a host cell or if the gene of the present invention is surely expressed in a host cell. For instance, a gene deficient in a host cell is used as a marker and plasmid etc. comprising the marker and the gene of the present invention is introduced as an expression vector into a host cell. Thereby, the introduction of the gene of the present invention may be verified by the expression of the marker gene. Alternatively, the antibody of the present invention or a fragment thereof and a marker protein may be expressed as a fusion protein. For instance, Green Fluorescent Protein (GFP) derived from *Aequorea victoria* may be used as a marker and the antibody of the present invention or a fragment thereof may be expressed as a GFP fusion protein.

The above host cell is not particularly limited but a variety of known cells may suitably be used. Specifically, the host cell includes, but not particularly limited to, an animal cell including cells from human or mouse, *Caenorhabditis elegans*, an oocyte of *Xenopas laevis*, a culture cell of a variety of mammals (rat, rabbit, pig, monkey, etc.), a culture cell of insects such as *Drosophila melanogaster* or silkworm moth, bacteria such as *Escherichia coli*, yeast (budding yeast (*Saccharomyces cerevisiae*) and fission yeast (*Schizosaccharomyces pombe*)) and the like.

A method for introducing a recombinant expression vector into a host cell, i.e. a method for transfection, is not particularly limited but the conventional known methods such as electroporation, calcium phosphate method, liposome method and DEAE-dextran method may suitably be used.

A transformant of the present invention is a transformant where the gene of the above item 2, i.e. the gene coding for the antibody or a fragment thereof of the above item 1, is introduced. As used herein, "a gene is introduced" means that a gene is introduced expressibly into a cell of interest (host cell) by known genetic engineering techniques (gene manipulation techniques). The term "transformant" refers to not only a cell, a tissue or an organ but also an animal individual. An animal of interest is not particularly limited but includes mammals such as cow, pig, sheep, goat, rabbit, dog, cat, guinea pig, hamster, mouse and rat. In particular, rodents such as mouse and rat are widely used as an experimental animal and a disease animal model. Among them, mouse is preferable as an experimental animal and a disease animal model since many inbred strains have been created and techniques of culture of fertilized eggs and in vitro fertilization have been completed.

The antibody or a fragment thereof of the above item 1 can be prepared with the transformant of the present invention which is prepared using the expression vector of the present invention.

4. Utilization of Humanized Antibody of the Present Invention or a Fragment Thereof The antibody of the present invention specifically recognizes TTR with structural change (e.g. TTR amyloid), inhibits fibrillization of TTR and exerts the preventive effect against FAP. Thus, the present invention includes a device for detecting structural change of TTR, a diagnostic agent for TTR amyloidosis (in particular, FAP), a medicament for inhibiting fibrillization of TTR, and a pharmaceutical composition for preventing and/or treating TTR amyloidosis (in particular, FAP).

The present invention includes a device for detecting structural change of TTR comprising the antibody of (1) or a fragment thereof (a detection device for TTR amyloid). The detection device of the present invention includes, for instance, an antibody chip or an antibody column etc. in which an antibody that specifically binds to TTR with structural change or a fragment thereof is immobilized on a basement (carrier). The detection device of the present invention, for instance, may be used for detecting TTR with structural change (e.g. TTR amyloid) contained in a sample such as blood or urine. Besides, the detection device of the present invention may also be used for diagnostic or therapeutic application for determining diseases associated with TTR with structural change (e.g. TTR amyloid) or for evaluating the therapeutic effect.

The present invention further includes a carrier used for removal of TTR amyloid comprising the antibody of (1) or a fragment thereof (a carrier for removal of TTR amyloid). This carrier for removal may be prepared by binding by a usual method the antibody and the like to a carrier that is normally used in chromatography. The above carrier for removal is used in such a manner that blood is taken from patients suffering from amyloidosis caused by TTR amyloid and is passed through a column filled up with the carrier for removal to thereby remove TTR amyloid in blood.

Furthermore, the present invention includes a reagent for detecting TTR amyloid comprising the antibody or a fragment thereof of the above item 1 (a reagent for detecting TTR amyloid). Thus, when label immunoassay such as radioimmunoassay, enzyme immunoassay and fluorescent immunoassay is applied, TTR in a test sample can qualitatively or quantitatively be analyzed in a rapid and accurate manner. In the label immunoassay, the above antibody or a fragment thereof is used with a label of e.g. a radioactive substance, an enzyme and/or a fluorescent substance. Besides, the antibody or a fragment thereof specifically reacts with TTR amyloid to show an immune reaction and therefore the measurement of the immune reaction with the labelling substance as an index allows for detection of small quantities of TTR amyloid present in a test sample at high precision. Label immunoassay, as compared to bioassay, is characterized by that a large number of test samples can be analyzed at a time, that time and labor for analysis is small, and that analysis is at high precision.

The present invention includes a diagnostic agent for TTR amyloidosis comprising the antibody or a fragment thereof of the above item 1. A method for diagnosing the disease of the present invention comprises measuring an amount of TTR amyloid in a test sample (blood, body fluid, tissue etc.) and diagnosing the disease in accordance with the results of the measurement. The disease of interest includes the one caused by TTR amyloid, including Senile Systemic Amyloidosis (SSA) and Familial Amyloidotic Polyneuropathy (FAP).

The antibody of the present invention proved to show the effect to suppress fibrillization of TTR. Therefore, the present invention includes a medicament for inhibiting fibrillization of TTR comprising the antibody or a fragment thereof of the above item 1 (a fibrillization inhibitor). The fibrillization inhibitor may contain pharmaceutically acceptable additives such as one or more kinds of excipients, one or more kinds of binding agents, one or more kinds of disintegrating agents, one or more kinds of lubricants and one or more kinds of buffers.

The antibody of the present invention proved to show the effect when administered to a model animal of TTR amyloidosis. Therefore, the present invention includes a pharmaceutical composition for preventing and/or treating TTR amyloidosis comprising the antibody or a fragment thereof of the above item 1. The pharmaceutical composition may contain pharmaceutically acceptable additives such as one or more kinds of excipients, one or more kinds of binding agents, one or more kinds of disintegrating agents, one or more kinds of lubricants and one or more kinds of buffers.

The present invention is further explained in more detail by means of the following Examples but is not construed to be limited thereto.

When the commercially available kits or reagents are used, the experiments were performed in accordance with protocol attached thereto unless otherwise mentioned.

Example 1

Conjugation of TTR Peptide

Peptides where cysteine was added at the N terminal or the C terminal of human TTR115-124 peptide (SEQ ID NO:9) were prepared by chemical synthesis (outsourced to SIGMA-ALDRICH). TTR115-124 with addition of cysteine at the N terminal is hereinafter referred to as "TTR02 peptide" whereas TTR115-124 with addition of cysteine at the C terminal is referred to as "TTR03 peptide". Using Immunogen EDC Kit with mcKLH and BSA (Thermo), KLH or BSA was conjugated to the cysteine at the N terminal or the C terminal of TTR02/TTR03 peptides.

Example 2

Biotinylation of TTR Peptide

Using Biotin-PE-maleimide (DOJINDO), the two peptides synthesized in Example 1, TTR02 and TTR03 peptides, were biotinylated. TTR02 and TTR03 peptides after biotinylation were purified by gel filtration in PBS (SIGMA) using Superdex peptide (GE Healthcare) to prepare biotinylated TTR peptides.

Example 3

Preparation of Anti-Human TTR Monoclonal Antibody

KLH-conjugated TTR02 peptide (100 μg/mL) and Freund's Complete Adjuvant (DIFCO) were mixed at 1:1 and TTR knockout mouse (Non-patent reference 7, donated from Kumamoto University) was immunized with 200 μL of the mixture. More than 2 weeks after the first immunization, KLH-conjugated TTR02 peptide and Freund's InComplete Adjuvant (DIFCO) were mixed and the mouse was immunized with the mixture. After immunization, blood was sampled at each 1 to 2 weeks and the mouse continued to be immunized under the same conditions as above until sufficient increase in antibody titer was attained. Antibody titer was confirmed by ELISA.

After sufficient increase in antibody titer was confirmed, the spleen cells were collected from the mouse and fused with mouse myeloma cells P3U1 by PEG technique. The cells after fusion were suspended in HAT medium and inoculated in 96-well Plate. By continued culture in HAT medium, hybridomas alone were selected. At Day 7 to Day 11 after the inoculation, the binding activity to human TTR of the antibodies contained in the culture supernatant was evaluated by the method shown below.

Example 4

Binding Activity Test of Anti-TTR Antibody

The antigen binding activity of the antibodies of the obtained hybridomas was evaluated by ELISA. The BSA-conjugated TTR02, TTR03 peptides prepared in Example 1 were diluted with PBS (SIGMA) at 2 μg/mL. Each 100 μL/well of the diluent was added to Maxisorp Plate (Nunc) and incubated at room temperature for 1 hour to immobilize the TTR peptides. Each 300 μL/well of 1% BSA-PBS was added to the immobilized plate and incubated at room temperature for 1 hour for blocking the plate. Each 100 μL of the culture supernatant of the obtained hybridomas was added to each well of the plate and incubated at 37° C. After 1 hour, the well was washed with PBST and each 100 μL of the detection antibody anti-mouse IgG(H+L)/HRP (Zymed) diluted 5,000-folds with 1% BSA-PBS was added to each well of the plate and incubated at 37° C. After 1 hour, the well was washed with PBST and each 100 μL of TMB (SIGMA) was added to each well of the plate for development. After 30 minutes, the reaction was quenched with 1N sulfuric acid and color development value (O.D. 450 nm/650 nm) was measured with a microplate reader (Molecular Devices).

As a result, an excellent binding activity to the TTR peptides was found in hybridoma T24.

Example 5

Obtainment of Anti-TTR Antibody Gene

For hybridoma T24 expressing antibodies having the binding activity to the TTR peptides, cloning of the hybridoma was conducted by limiting dilution. Using the hybridoma 1×10$^7$ cells after cloning as a starting material, total RNAs were extracted using TRIzol (Invitrogen). Using the total RNAs as a template, First-strand cDNAs were prepared using random primer (Invitrogen), Ready-To-Go You-Prime First-Strand Beads (GE Healthcare). Then, using the cDNAs as a template, VH and VL gene fragments were amplified with Ex-Taq (Takara) using a primer to the leader region and a primer to the J region designed by referring to classification of the sequences of the V region and the J region by Kabat et al. (Sequences of Proteins of Immunological Interest 4th ed., Public Health Service, NIH, Washington D.C., 1987). The DNAs of the amplified VH region and VL region were TA cloned into pCR2.1-TOPO (Invitrogen) to give the gene sequence of anti-TTR antibody. The DNA nucleotide sequence of the cloned T24 antibody was determined using Big Dye Terminator v3.1 Cycle sequencing kit (Applied Biosystems) and Genetic analyzer ABI Prism 3100 (Applied biosystems).

Example 6

Construction of Mouse T24 Antibody Expression Vector

Based on the sequence obtained in Example 5, T24 antibody expression vector was constructed. For the VH region, using as a template the vector with T24VH inserted therein constructed in Example 5, the VH region was amplified by PCR with primestar GXL (Takara) using T24VH-Fw primer (SEQ ID NO:10) and T24VH-Rv primer (SEQ ID NO:11). For the VL region, using as a template the vector with T24VL inserted therein, the VL region was similarly amplified using T24VL-Fw primer (SEQ ID NO:12) and T24VL-Rv primer (SEQ ID NO:13) and purified with QIAquick PCR Purification Kit (QIAGEN). The amplified VH region fragment and the amplified VL region fragment were introduced into vector pKMA010-mCg1 treated with XhoI/NruI and vector pKMA009-mCk treated with XhoI/BamHI, respectively, with In-fusion Enzyme (Clontech) to construct a vector expressing T24 antibody with mouse constant region (hereinafter referred to as "mouse T24 antibody"), H chain expression vector pKMA010-T24-mCg1 and L chain expression vector pKMA009-T24-mCk (FIG. 1). The vector pKMA010-T24-mCg1 has the sequence of mouse T24 antibody H chain downstream CAG promoter and DHFR gene as a drug resistance gene. The vector pKMA009-T24-mCk is the one where the sequence of mouse T24 antibody L chain is inserted downstream CAG promoter. The vectors pKMA010-T24-mCg1 and pKMA009-T24-mCk are collectively referred to as "mouse T24 antibody expression vector".

Example 7

Humanization of T24 Antibody

The obtained anti-TTR antibody was humanized by CDR Grafting to prepare RT24 antibody. CDRs 1-3 in the VH region or the VL region of T24 antibody were determined by the Kabat numbering scheme. The amino acid sequences and the nucleotide sequences of said CDRs 1-3 are shown in SEQ ID NOs:1-6. Amino acid sequences were designed where the amino acid sequences of T24 CDRs 1-3 were grafted to the amino acid sequences of the VH region or the VL region of a human antibody. Besides, amino acid sequences were also designed where the amino acid sequences of T24 CDRs 1-3 were grafted to the amino acid sequences of the VH region or the VL region of a human antibody and several amino acid residues were modified in framework regions of the VH region or the VL region. Nucleotide sequences coding for these amino acid sequences were chemically synthesized (outsourced to Takara Bio Inc.). One of these antibodies is referred to as "RT24 antibody" and the amino acid sequence of its VH region or VL region are shown in SEQ ID NOs:7 and 8. A vector expressing RT24 antibody with human constant regions (hereinafter referred to as "human RT24 antibody") was constructed as described below. A plasmid containing the chemically synthesized RT24 was digested with HindIII and BamHI to cleave the region containing the sequences coding for the VH region and the VL region of RT24 antibody. The cleaved VH sequence of the RT24 antibody was introduced into pUC-hCγ (expression vector pUC19 with human Cγ1 gene inserted therein; restriction enzyme sites SalI, HindIII and BamHI are inserted upstream human Cγ1 gene and restriction enzyme site SalI is inserted downstream human Cγ1 gene) previously digested with HindIII and BamHI to give pUC-RT24-hCγ1. Likewise, the cleaved VL sequence of the RT24 antibody was introduced into pUC-hCκ (expression vector pUC19 with human Cκ gene inserted therein; restriction enzyme sites SalI, HindIII and BamHI are inserted upstream human Cκ gene and restriction enzyme site SalI is inserted downstream human Cκ gene) previously digested with HindIII and BamHI to give pUC-RT24-hCκ. pUC-RT24-hCγ1 was treated with SalI and introduced into expression vector pCAGG-S1(Sal).dhfr.neo (Patent reference 2) previously treated with SalI to construct human RT24 antibody H chain expression vector pCAGGS1.dhfr.neo-RT24-hCg1. pUC-RT24-hCκ was treated with SalI and introduced into expression vector pCAGG-S1(Sal) (Patent reference 2) previously treated with SalI to construct human RT24 antibody L chain expression vector pKMA009-RT24-hCk. The vector pCAGGS1.dhfr.neo-RT24-hCg1 has the sequence of human RT24 antibody VH region and the human Cγ1 gene downstream CAG promoter and DHFR gene and neomycin resistant gene as a drug resistance gene. The vector pKMA009-RT24-hCk is the one where the sequences of human RT24 antibody VL region and the human Cκ gene are inserted downstream CAG promoter. The vectors pCAGGS1.dhfr.neo-RT24-hCg1 and pKMA009-RT24-hCk are collectively referred to as "human RT24 antibody expression vector".

Then, construction of a vector expressing RT24 antibody having mouse constant regions (hereinafter referred to as "chimeric RT24 antibody") was performed. For the VH region, using pCAGGS1.dhfr.neo-RT24-hCg1 as a template, the VH region was amplified by PCR with primestar GXL (Takara) using pCAG-Fw primer (SEQ ID NO:14) and T24VH-Rv primer. For the VL region, pKMA009-RT24-hCk was treated with XbaI and BamHI to cleave a region containing RT24 VL region. The amplified VH region fragment and the amplified VL region fragment were introduced into vector pKMA010-mCg1 treated with XbaI and NruI and vector pKMA009-mCk treated with BamHI, respectively, with In-fusion Enzyme (Clontech) to construct chimeric RT24 antibody H chain expression vector pKMA010-RT24-mCg1 and chimeric RT24 antibody L chain expression vector pKMA009-RT24-mCk. The vector pKMA010-RT24-mCg1 has the sequence of human RT24 antibody VH region and mouse Cγ1 gene downstream CAG promoter and DHFR gene as a drug resistance gene. The vector pKMA009-RT24-mCk is the one where the sequence of human RT24 antibody VL region and mouse Cκ gene are inserted downstream CAG promoter. The vectors pKMA010-RT24-mCg1 and pKMA009-RT24-mCk are collectively referred to as "chimeric RT24 antibody expression vector".

Freestyle293F cells (Invitrogen) were transfected with mouse T24 antibody expression vector, chimeric RT24 antibody expression vector or human RT24 antibody expression vector using Neofection (ASTEC Co., Ltd.) and were subject to shaking culture at 37° C. under environmental conditions of 8% $CO_2$ at 125 rpm for expression of mouse T24 antibody, chimeric RT24 antibody or human RT24 antibody. On the fifth day of culture, the culture supernatant was collected and purified by chromatography using HiTrap rProteinA FF (GE Healthcare). The elution fraction containing mouse T24 antibody, chimeric RT24 antibody or human RT24 antibody was dialyzed against PBS (SIGMA) to provide the purified form of mouse T24 antibody, chimeric RT24 antibody or human RT24 antibody.

Example 8

Cloning of Human TTR Gene

For constructing a human TTR expression vector, cloning of a human TTR gene was performed. Using Human liver Marathon-Ready cDNA (Clontech) as a template, PCR was conducted using primers (TTR-F2: SEQ ID NO:15 and TTR-R: SEQ ID NO:16), designed at the 5'-end and the 3'-end of mature TTR, and Ex-Taq (Takara). After TA cloning of the PCR products into pCR2.1-TOPO, the nucleotide sequence of a human TTR gene was confirmed by sequence analysis. After confirming that the sequence was correct, pCR2.1-TOPO where the TTR gene was inserted was treated with BamHI and HindIII to cleave a region containing the sequence coding for the TTR gene. The cleaved sequence was introduced into pQE-30 (QIAGEN) previously treated with BamHI and HindIII to construct a wild-type human TTR expression vector.

Example 9

Construction of Human TTR Mutant Expression Vector

Using as a template the wild-type human TTR expression vector constructed in Example 8, point mutation of an amino acid was introduced using site-directed mutagenesis. Point mutation of an amino acid was conducted for each of 17 kinds of mutations D18G, V30M, E54K, L55P, Y114C, S115A, Y116A, S117A, T118A, T119A, A120S, V121I, V122A, V122I, T123A, and N124A. The sequences coding for the above 17 kinds of the TTR mutants were introduced into pQE-30.

Example 10

Epitope Analysis of RT24 Antibody

For more fully analyzing the epitope of RT24 antibody, the reactivity analysis of RT24 antibody was performed using the alanine-substitution variant of TTR115-124 peptide region used for creating said antibody. *E. coli* strain M15 was transfected with the TTR variant expression vector constructed in Example 9 and cultured in 20 mL of LB/Ampicillin (50 μg/mL)/Kanamycin (25 μg/mL) at 37° C. At the point of O.D.600 nm=0.5, IPTG was added at a final concentration of 10 mM and the culture was continued overnight. The culture was centrifuged and the precipitate fraction was solubilized with Bugbuster (Merck). The solubilized cell suspension was electrophoresed on 8-16% SDS-PAGE gel and transferred to Immobilon-P (Millipore) from the gel. The transferred membrane was added with 2% Skimmilk-PBST and shaken at room temperature for 1 hour for blocking the membrane. Chimeric RT24 antibody was diluted with 2% Skimmilk-PBST at a concentration of 1 μg/mL and the membrane was added with 10 mL of the diluent and shaken at room temperature for 1 hour. The membrane was washed with PBST, added with a detection antibody HRP-labelled anti-mouse IgG(H+L) (AMERICAN QUALEX INTERNATIONAL), which was previously diluted 5,000-folds with 2% Skimmilk-PBST, and was shaken at room temperature for 1 hour. After washing with PBST, color development was conducted with Ez West Blue (ATTO).

Figure 2:
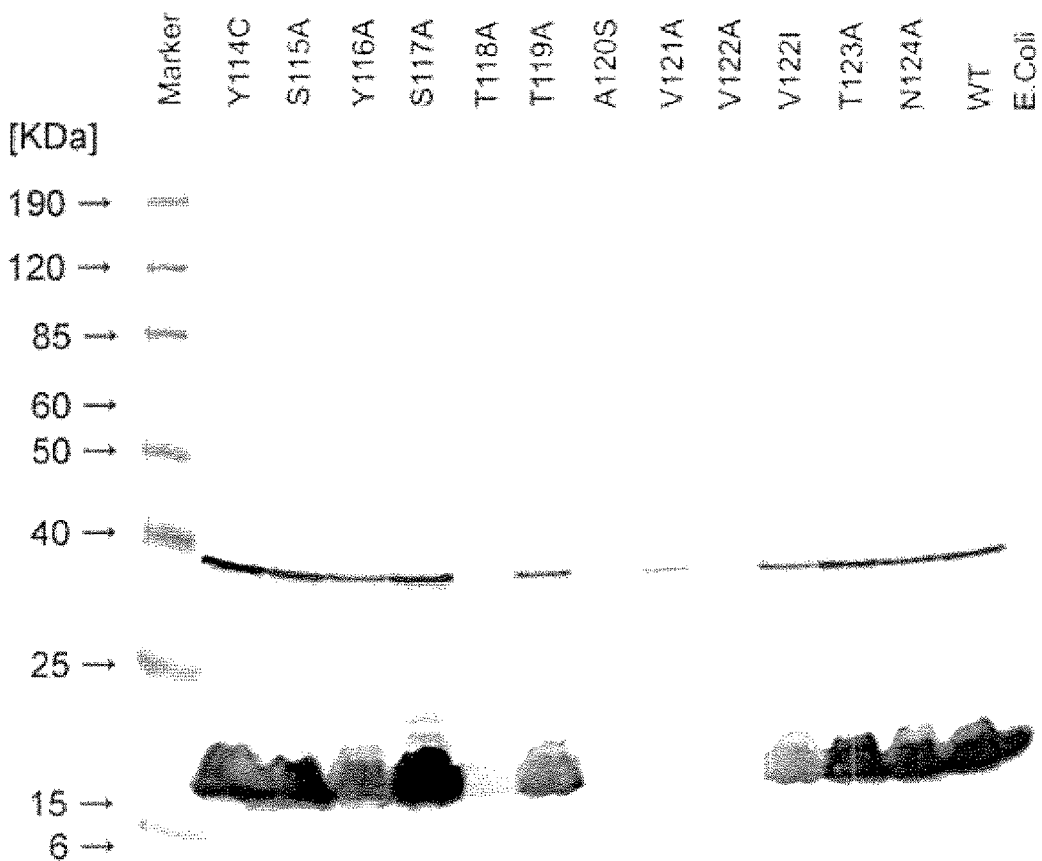
FIG. 2 shows the results of epitope analysis.

As a result, as shown in FIG. 2, it was found that RT24 antibody had an epitope within TTR115-124 positions, among others, at positions 118-122.

Example 11

Preparation of Purified Recombinant TTR

Referring to Matsubara et al. (Non-patent reference 13), a purified recombinant TTR was prepared. *E. coli* strain M15 was transfected with expression vectors expressing wild-type TTR, or D18G, V30M, E54K, L55P, Y114C, Y116S, V122I TTR variants constructed in Examples 8 and 9 and cultured with 20 mL of LB/Ampicillin (50 μg/mL)/Kanamycin (25 μg/mL) at 37° C. At the point of O.D.600 nm=0.5, IPTG was added at a final concentration of 10 mM and culture was continued overnight. The cells were collected from the culture by centrifugation and suspended in Buffer A (50 mM PB+0.3 M NaCl+10 mM Imidazole+20 mM 2-Mercaptoethanol). The suspension was sonicated for 15 minutes and then centrifuged to collect supernatant. The supernatant was subject to His-tag purification with Ni-NTA Agarose (QIAGEN) and the eluent fraction containing the recombinant TTRs was dialyzed against 20 mM $NaHCO_3$. The recombinant TTRs after dialysis were purified by gel filtration with Superdex 75 (GE Healthcare) using 10 mM PB (pH7.5) and a fraction of tetrameric TTR was used as purified recombinant TTRs.

Example 12

Reaction Specificity Analysis of RT24 Antibody

For analyzing the reactivity of RT24 antibody to TTR tetramer, reaction specificity analysis was performed using surface plasmon resonance. The purified V30M TTR prepared in Example 11 was diluted with 10 mM PB (pH 7.5) at 3 mg/mL and mixed with a solution of an equivalent amount of 200 mM acetate buffer+100 mM NaCl (pH 3.0) up till a concentration of 1.5 mg/mL and the mixture was reacted in an incubator at 37° C. for 16 hours to prepare V30M TTR fibril. For TTR after the reaction, fibrillization was confirmed by ThioflavinT assay. ThioflavinT assay was performed by diluting TTR with 50 mM Glycine-NaOH Buffer (pH 9.5) so that ThioflavinT was at 20 µM and TTR was at 30 to 60 µg/mL and measuring fluorescence intensity with spectrofluorometer FP-6500 (JASCO) (excitation wavelength 440 nm, fluorescent wavelength 480 nm).

Using Biacore2000 (GE Healthcare), each around 1,000 RU of WT TTR tetramer, V30M TTR tetramer and V30M TTR fibril (all recombinants) was immobilized on Sensorchip CM5 (GE Healthcare). Immobilization of the ligand was performed with 10 mM acetate buffer (pH 6.0). Polyclonal Rabbit Anti-Human Prealbumin (Dako), RT24 antibody and negative control antibody, which were diluted with HBS-EP Buffer at 10 µg/mL, were migrated at 20 µL/min for 2 minutes. After migration, dissociation was carried out for 60 minutes and regeneration was performed with 10 mM Gly-NaOH (pH 9.0) for 30 seconds.

Figure 3:
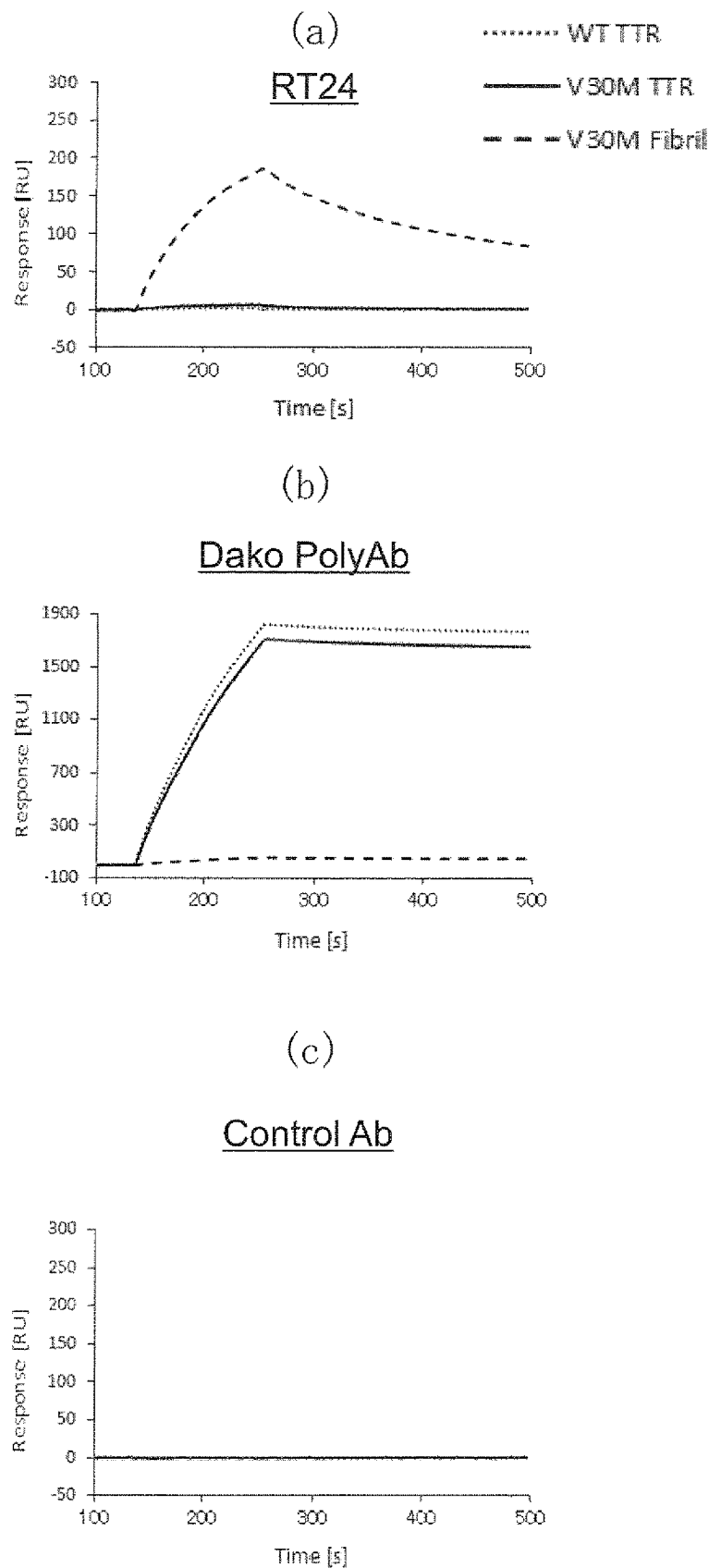
FIG. 3 shows the results of reaction specificity analysis using surface plasmon resonance for (a) RT24 antibody, (b) polyclonal antibody manufactured by Dako, and (c) negative control antibody, respectively.

As a result, as shown in FIG. 3, it was revealed that RT24 antibody did not react with WT TTR and V30M tetrameric TTRs but specifically recognized V30M fibril (a) Polyclonal antibody manufactured by Dako strongly reacted with WT TTR and V30M TTR and weakly reacted with V30M TTR fibril (b). Negative control antibody reacted with none of the TTRs (c).

Example 13

Reactivity Analysis of T24 Antibody to Patient Sera

Analysis was conducted to investigate whether T24 antibody shows the reactivity to sera from FAP patients. It is a preferable property for an antibody for FAP therapy that the administered antibody does not recognize human TTR in patient sera. The BSA conjugates of TTR02 and TTR03 peptides prepared in Example 1, sera from healthy adults and sera from FAP patients having V30M TTR variant at 2 µg/mL and fibril of wild-type TTR from sera treated at pH 3.0 as in Example 12 and TTR amyloid extracted from the spleen of FAP patients at about 4 µg/mL were added to Maxisorp plate (Nunc) at 100 µL/well for immobilization of the antigens. Each 300 µL/well of 1% BSA-PBS was added to the immobilized plate and incubated at room temperature for 1 hour for blocking the plate. T24 antibody was serially diluted with 1% BSA-PBS and each 100 µL of the diluent was added to each well of the plate and incubated at 37° C. After 1 hour, the well was washed with PBST and each 100 µL of the detection antibody anti-mouse IgG(H+L)/HRP (Zymed) was added to each well of the plate and incubated at 37° C. After 1 hour, the well was washed with PBST and each 100 µL of TMB (SIGMA) was added to each well of the plate for development. After 30 minutes, the reaction was quenched with 1N sulfuric acid and color development value (O.D. 450 nm) was measured with a microplate reader (Molecular Devices).

Figure 4:
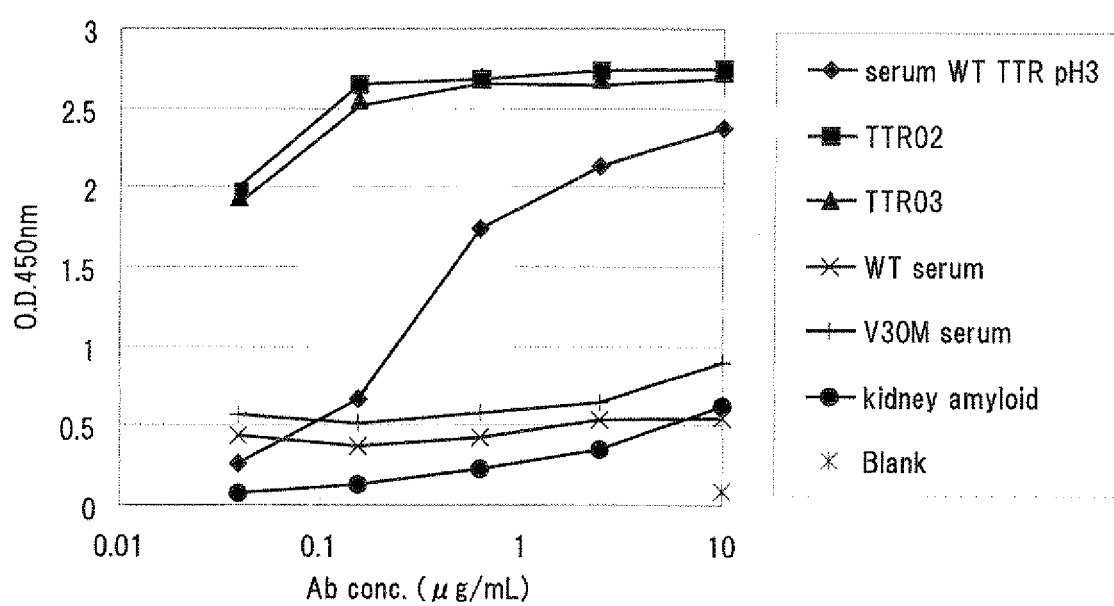
FIG. 4 shows the results of reactivity analysis to patient sera.

As a result, as shown in FIG. 4, T24 antibody clearly showed the reactivity to TTR peptide, TTR amyloid from FAP patients and to amyloid formed by acid treatment of wild-type TTR from sera in a concentration-dependent manner but not to sera from healthy adults and from FAP patients.

Example 14

Reactivity Analysis of T24 Antibody and Chimeric RT24 Antibody to Patient Tissues The heart was removed from FAP patients having V30M TTR and formalin fixed. The fixed heart tissue was embedded in paraffin block to prepare tissue section. After the tissue section was sliced to a thickness of 4 µm and attached to an object glass, deparaffinization treatment was conducted. After washing with PBS, the tissue section was infiltrated to 0.1% periodic acid dihydrate for 10 minutes and further washed with PBS. The tissue section was immersed in Rabbit serum (Dako) diluted 50-folds with 0.5% BSA-PBS for 1 hour for blocking. After washing with PBS, the tissue section was immersed in T24 antibody/chimeric RT24 antibody/negative control antibody as a primary antibody, which were diluted with 0.5% BSA-PBS to 10 µg/mL, at 4° C. overnight. The tissue section was then immersed in HRP-labelled Rabbit anti-mouse IgG (Dako) as a secondary antibody, which was diluted 100-folds with 0.5% BSA-PBS, at room temperature for 1 hour. After washing with PBS, development with DAB was conducted. Hematoxylin staining was also done. For positive control, the same procedures were performed using Polyclonal Rabbit Anti-Human Prealbumin (Dako) as a primary antibody and HRP-labelled Goat anti-Rabbit IgG (Dako) as a secondary antibody. Besides, taking into consideration the possibility that TTR is denatured by formalin fixation to thereby alter its steric structure, frozen tissue section of the heart of FAP patients having V30M TTR was also subject to immunostaining in like manner. Furthermore, for confirming the presence of amyloid fibril, Congo red staining was also conducted. Congo red is known to attach to amyloid fibril to thereby cause short-wavelength shift.

Figure 5:
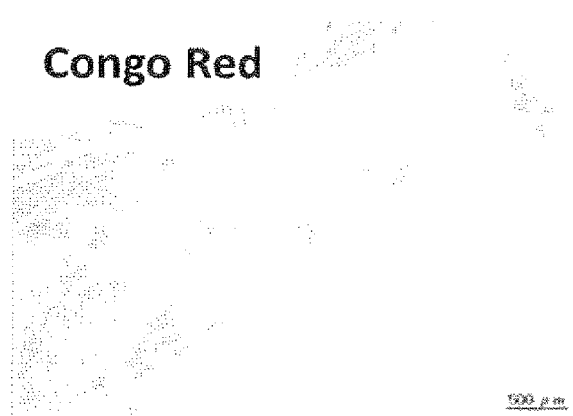
FIG. 5(a) shows the results of reactivity analysis to patient tissue (paraffin section).
FIG. 5(b) shows the results of reactivity analysis to patient tissue (frozen section).
Figure 5:
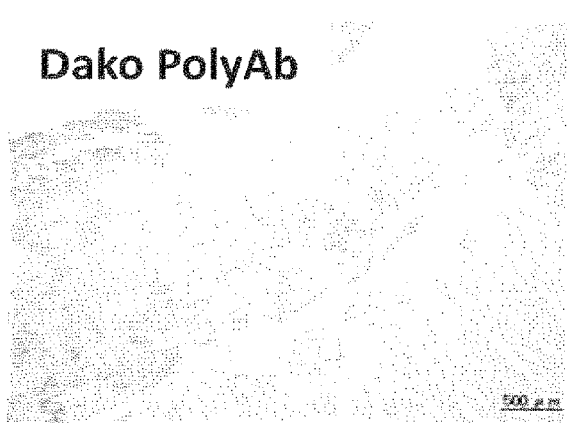
Figure 5:
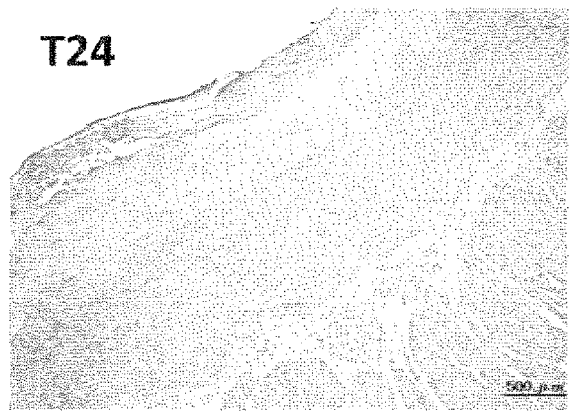
Figure 5:
Figure 5:
Figure 5:
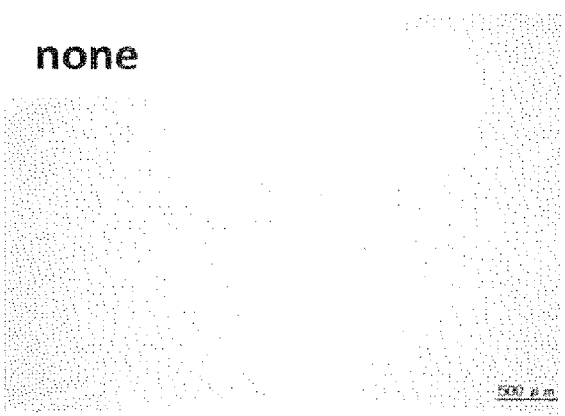
Figure 5:
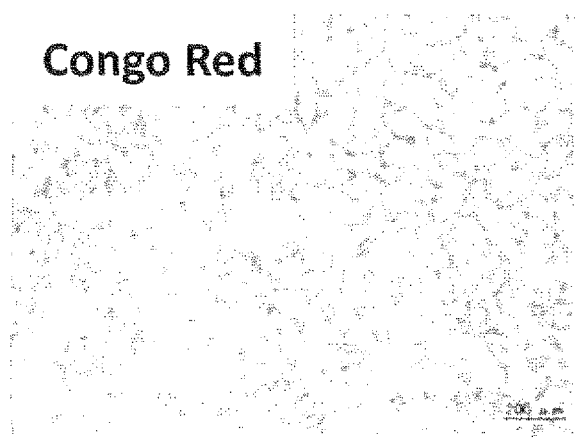
Figure 5:
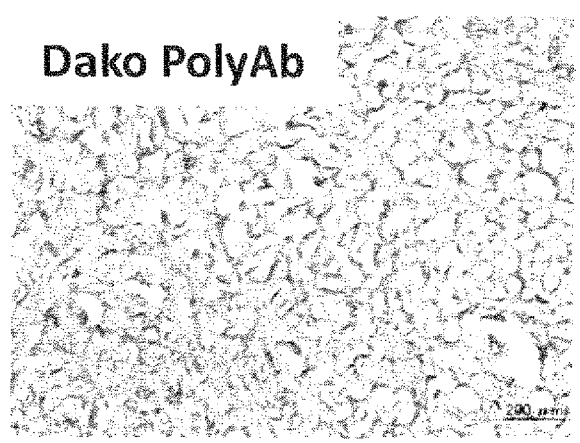
Figure 5:
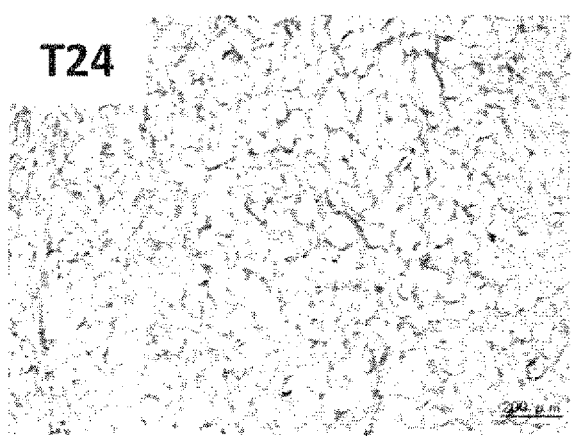
Figure 5:
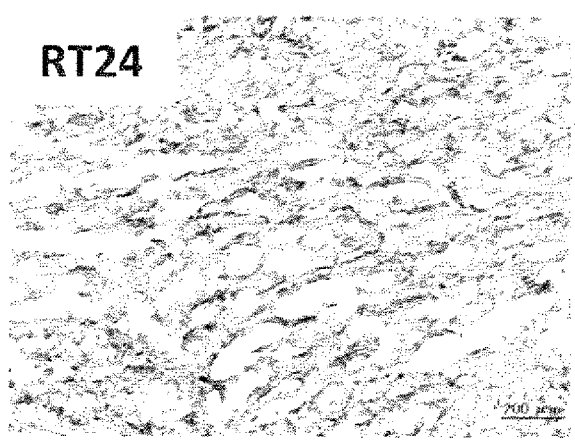
Figure 5:
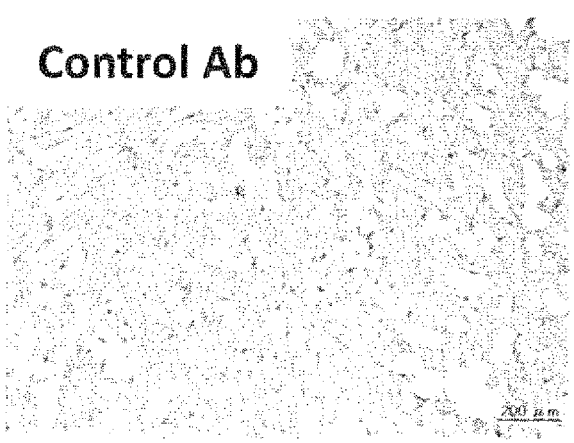
Figure 5:
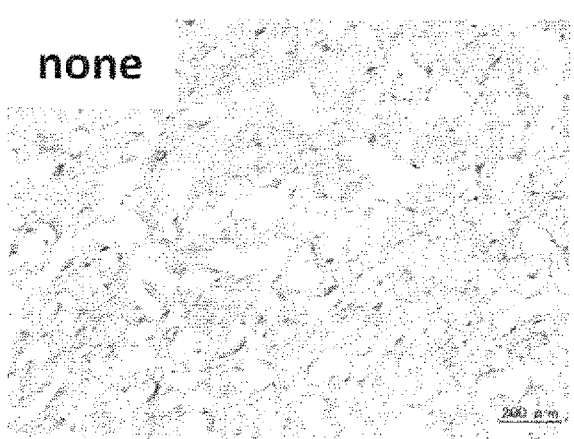

As a result, as shown in FIG. 5, it was confirmed that T24 antibody and chimeric RT24 antibody specifically recognized TTR deposited in the heart from FAP patients in both the paraffin section (FIG. 5*a*) and the frozen section (FIG. 5*b*).

Example 15

Reactivity Analysis of RT24 Antibody to TTR Fibril

Seven kinds of the purified TTR mutants prepared in Example 11, D18G, V30M, E54K, L55P, Y114C, Y116S and V122I, and the purified wild-type TTR were left to stand at 37° C. under environmental conditions of pH 3.0 as in Example 12 overnight to prepare various recombinant TTR fibrils. Each 1.5 µg of the recombinant TTRs was electrophoresed on 8-16% SDS-PAGE gel (two sheets). One of the sheets was silver stained with Silver stain KANTO III (KANTO CHEMICAL CO., INC.). The other sheet was transferred to Immobilon-P (Millipore) from the gel. The transferred membrane was added with 2% Skimmilk-PBST and shaken at room temperature for 1 hour for blocking the membrane. Chimeric RT24 antibody was diluted with 2% Skimmilk-PBST at a concentration of 1 μg/mL and the membrane was added with 10 mL of the diluent and shaken at room temperature for 1 hour. The membrane was washed with PBST, added with a detection antibody HRP-labelled anti-mouse IgG(H+L) (AMERICAN QUALEX INTERNATIONAL), which was previously diluted 5000-folds with 2% Skimmilk-PBST, and was shaken at room temperature for 1 hour. After washing with PBST, color development was conducted with Ez West Blue (ATTO).

Figure 6:
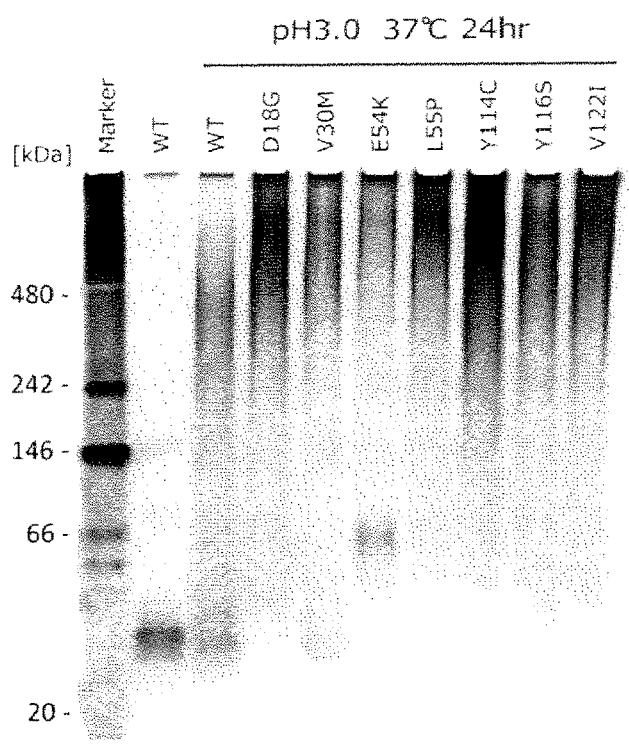
FIG. 6 shows the results of reactivity analysis to TTR fibril for (a) silver stain, and (b) Western blotting.
Figure 6:
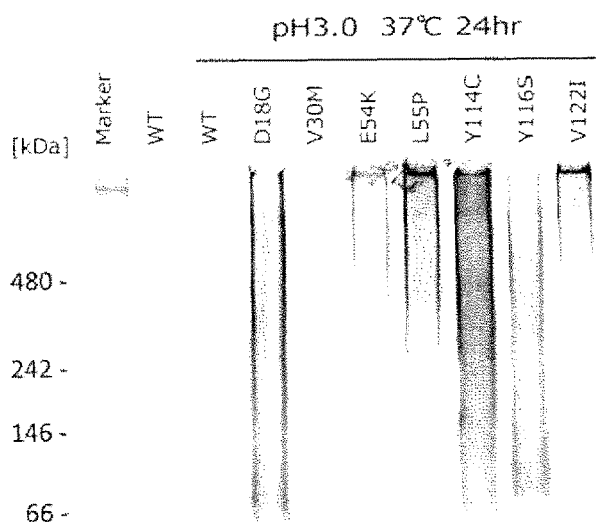

As a result, as shown in FIG. 6, it was found that RT24 antibody recognized various TTR fibrils but on the other hand did not recognize purified wild-type TTR not subject to fibrillization.

Example 16

Construction of Measurement System for Inhibitory Activity to V30M TTR-Fibrillization Recombinant V30M TTR was diluted with PBS(−) to 375 μg/mL and mixed with four kinds of surfactants at a final concentration of 0.1%, 0.01% and 0.001%. The surfactants used were (1) benzalkonium chloride (Yamazen Corporation), (2) sodium deoxycholate (Nacalai Tesque), (3) Zwittergent3-16 (Carbiochem), and (4) NP-40 (Wako). The mixtures were left to stand at 37° C. for 4 days and fluorescence intensity was measured by ThioflavinT assay (excitation wavelength 440 nm, fluorescent wavelength 480 nm) to evaluate a degree of TTR-fibrillization.

As a result of ThioflavinT assay, TTR-fibrillization progressed for any of the surfactants when used at a concentration of 0.1%. Among others, it was found that TTR-fibrillization progressed most rapidly when sodium deoxycholate was used. Next, an optimum concentration of sodium deoxycholate was investigated.

Recombinant V30M TTR was diluted with PBS(−) to 375 μg/mL and mixed with sodium deoxycholate at a concentration of 1%, 0.5%, 0.2%, 0.1% and 0.01%. The mixtures were left to stand at 37° C. and, after 4 days and 7 days, ThioflavinT assay was conducted to evaluate a degree of TTR-fibrillization.

As a result, it was found that the optimum concentration of sodium deoxycholate was 0.1%. Up till the present, the conditions under which fibrillization of V30M TTR progresses under the circumstance of neutral pH have not yet been reported and thus fibrillization of TTR was made to progress by placing TTR under acidic pH circumstances such as pH 3.0. On the other hand, since an antibody is denatured and loses its activity when it is exposed to acidic circumstances, it has been difficult to evaluate the inhibitory ability of anti-TTR antibody to TTR-fibrillization. In accordance with the present invention, it has newly been found that fibrillization of V30M TTR progresses even under neutral circumstances by introducing sodium deoxycholate into the system to thereby succeed in constructing the system which allows for evaluation of the inhibitory ability of anti-TTR antibody to fibrillization.

Example 17

V30M TTR-Fibrillization Inhibition Test of RT24 Antibody

Purified V30M TTR, and RT24 antibody or negative control antibody were mixed together at a molar ratio of 10 μM:0.01 to 2 μM (TTR: 550 μg/mL, antibodies: 1.5 to 300 μg/mL) and the mixture was left to stand under PBS+0.1% sodium deoxycholate at 37° C. for 3 days. Using the samples after being left to stand, ThioflavinT assay (excitation wavelength 440 nm, fluorescent wavelength 480 nm) was performed to measure fluorescence intensity.

Figure 7:
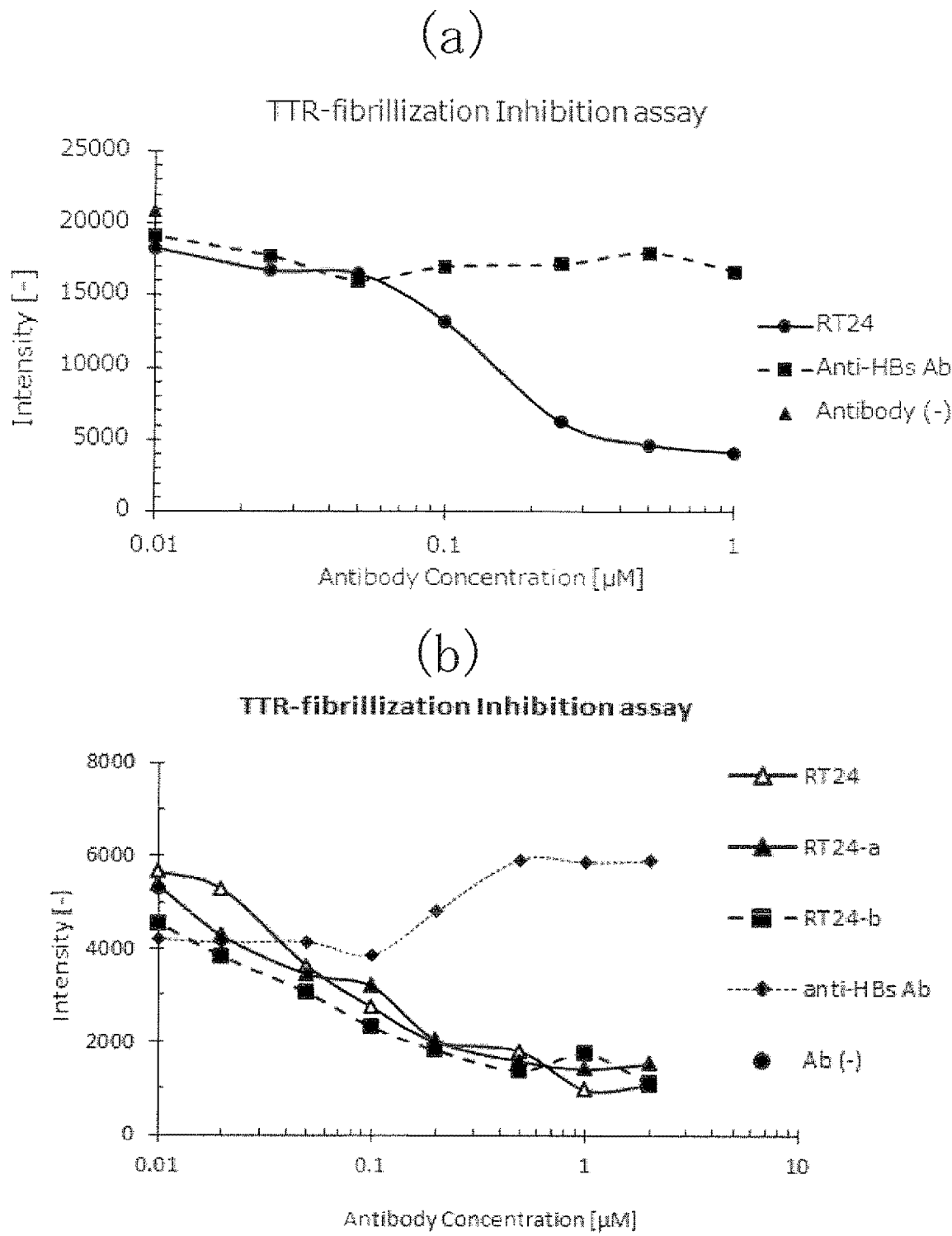
FIG. 7 shows the results of TTR-fibrillization inhibition test for (a) RT24 antibody, and (b) RT24-a antibody and RT24-b antibody, respectively.

As a result, as shown in FIG. 7, it was found that RT24 antibody had the activity to inhibit fibrillization of V30M TTR in an antibody concentration-dependent manner. Furthermore, the fibrillization inhibition test was also conducted for RT24-a and RT24-b, which were the antibodies where several amino acid residues in framework region of RT24 antibody were modified, to reveal that these antibodies had also the activity to inhibit fibrillization of V30M TTR as in the case of RT24. Since a system to evaluate the activity of anti-TTR antibody to inhibit TTR fibrillization has not yet been reported, RT24 antibody can be said to be the first antibody that has the activity to inhibit fibrillization of V30M TTR.

Example 18

Macrophage Phagocytic Ability Test

To investigate whether RT24 antibody promotes the ability of macrophage to phagocytose TTR fibril, macrophage phagocytic ability test was performed. This test mimics the process where macrophage removes TTRs deposited in the tissues of TTR patients. If the phagocytic ability of macrophage is promoted by the addition of RT24 antibody, it is expected that RT24 antibody has the activity to promote removal of TTR deposition in human tissues.

Human iPS cells were prepared from the skin tissue from healthy adults in accordance with the method described in Non-patent reference 17 and further differentiated into macrophages (iPS-MP). iPS-MPs (1 to $2\times10^6$ cells) were cultured in the presence of 50 ng/mL hGM-SCF and 25 pg/mL M-CSF in 10 cm dish for 24 hours. iPS-MPs were washed with PBS, then incubated in a medium containing 20 μg/mL of mitomycin C at 37° C. for 10 minutes to suspend the cell proliferative ability and added to 96-well plate at $5\times10^4$ cells/100 μL/well. V30M TTRs, untreated or acid treated for 24 hours, were diluted with the culture medium to 3.2 μg/mL and each 50 μL of the dilution was added. In addition, PBS/RT24 antibody/negative control antibody were diluted to 40 μg/mL and each 50 μL was added. Culture was continued at 37° C. under 5% $CO_2$ for 3 days and thereafter culture supernatant was collected.

A residual quantity of TTR after culture was quantified by ELISA as described below to evaluate the phagocytic ability of macrophage. A 96-well plate was added with each 5 μL of the culture supernatant and with 100 μL of a coating solution (25 mM sodium carbonate buffer) and thereafter was left to stand at 4° C. overnight. After washing with PBST, 250 μL of a blocking solution (a solution of 0.5% gelatin dissolved in the coating solution) was added and the plate was incubated at room temperature for 1 hour. After washing with PBST, Polyclonal Rabbit Anti-Human Prealbumin (Dako) was diluted 1,000-folds with 0.05% gelatin-PBST, each 100 μL of the dilution was added and the plate was incubated at room temperature for 1 hour. After washing with PBST, HRP-labelled Goat anti-Rabbit IgG (Dako) was diluted 5,000-folds with 0.05% gelatin-PBST, each 100 μL of the dilution was added and the plate was incubated at room temperature for 1 hour. After washing with PBST, development was performed with 100 μL of SureBlue (KPL) for 5 minutes and stopped with 100 μL of 1 M hydrochloric acid. A wavelength at 450 nm was measured with xMARK microplate reader (Bio-Rad Laboratories).

Figure 8:
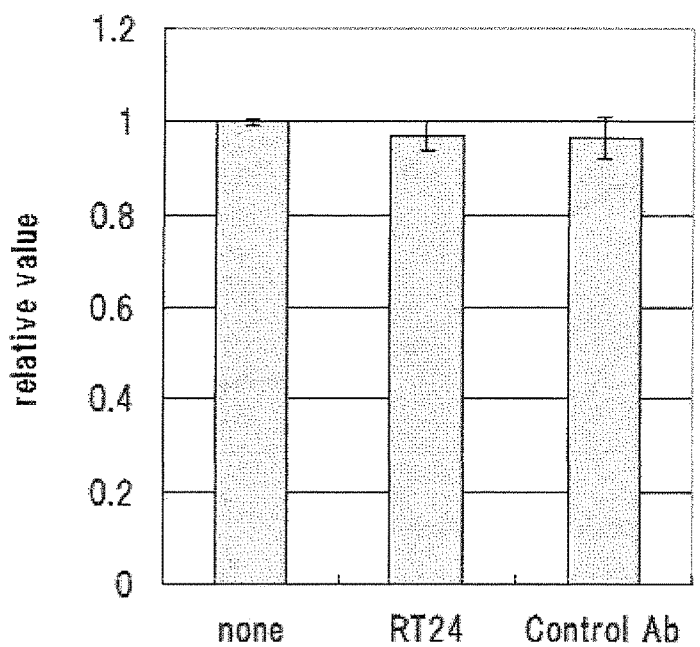
FIG. 8 shows the results of macrophage phagocytic ability test for (a) untreated purified V30M, and (b) TTR fibril, respectively.
Figure 8:
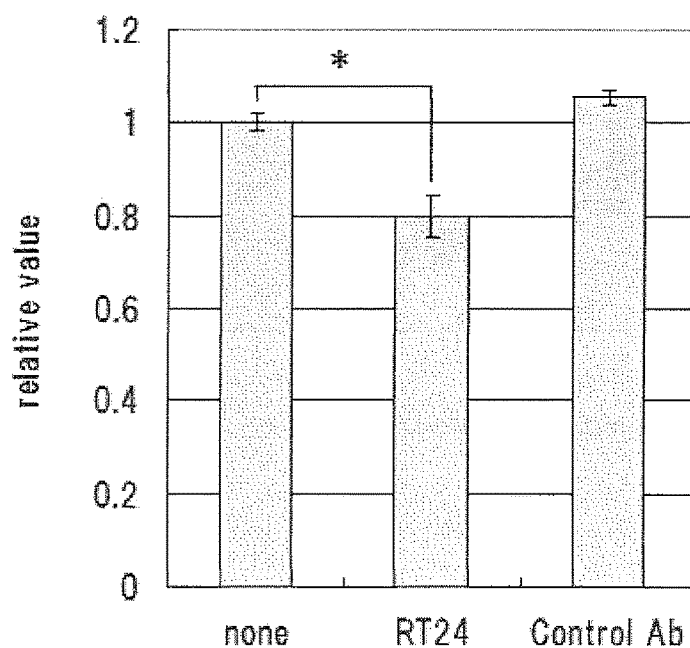

The results are shown in FIG. 8. For untreated purified V30M, no statistically significant difference in a residual quantity of TTR could be seen between the samples (a). To the contrary, it was found that, for TTR fibril, statistically significant reduction in a residual quantity of TTR was observed for RT24 antibody as compared to PBS (none) (b), demonstrating that RT24 antibody had the activity to promote the phagocytic activity of iPS cell-differentiated macrophages to TTR fibril.

Example 19

Drug Efficacy Evaluation Test Using V30M Tg Rat

Using V30M Tg rat (Non-patent reference 14; transgenic rat where a gene of human TTR with mutation of valine at position 30 to methionine in the amino acid sequence of TTR is introduced), 10 mg/kg of mouse T24 antibody or PBS was administered for 6 months, from 3-month old to 9-month old, each group consisting of 4 rats, once per week 26 times in total. After administration, the large intestine was taken out by autopsy and formalin fixed. The fixed tissue of the large intestine was embedded in a paraffin block to prepare tissue section. The tissue section was subject to immunostaining using Polyclonal Rabbit Anti-Human Prealbumin (Dako) as a primary antibody and HRP-labelled Goat anti-Rabbit IgG (Dako) as a secondary antibody and a degree of TTR deposition in the muscular layer of the large intestine was digitized and compared between the groups.

Figure 9:
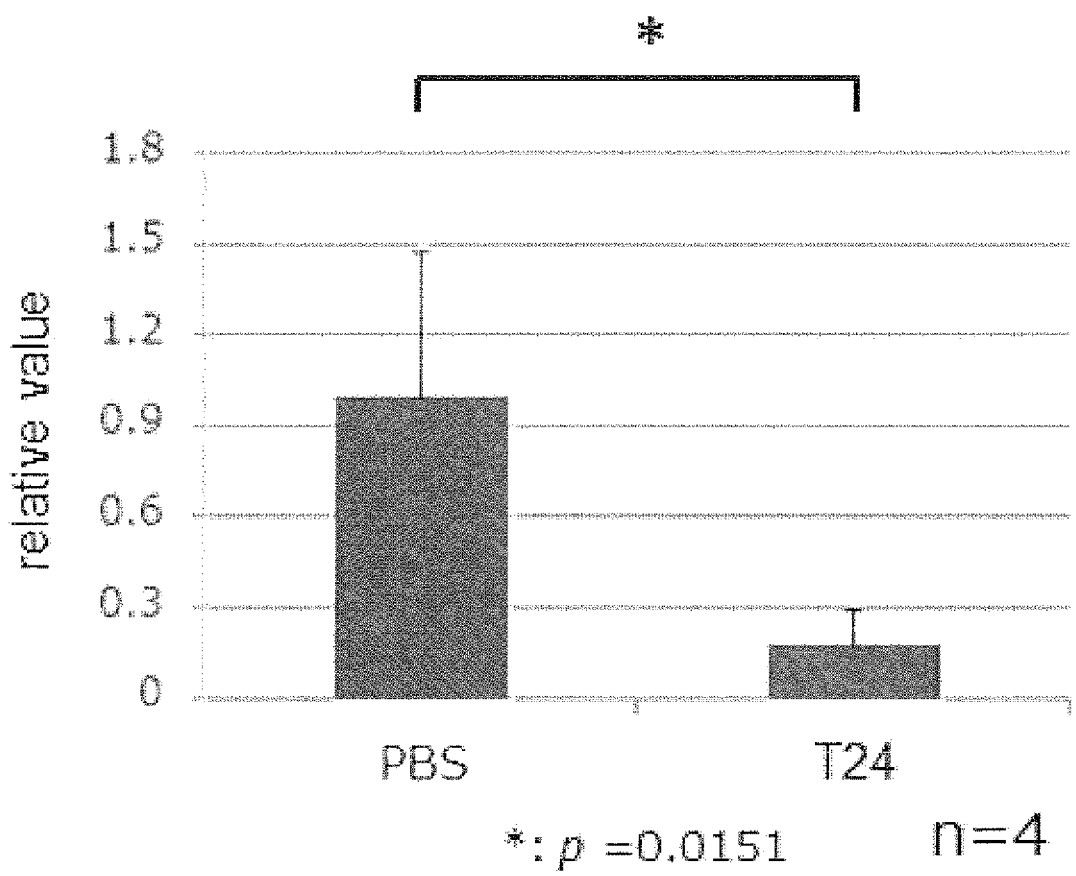
FIG. 9 shows the results of drug efficacy evaluation test using V30M Tg rat.

As a result, as shown in FIG. 9, TTR deposition was significantly suppressed in the group of RT24 antibody administration as compared to the group of PBS administration.

INDUSTRIAL APPLICABILITY

The humanized anti-transthyretin antibody of the present invention, as being excellent in its activity (the inhibitory activity to TTR fibrillization, the activity to promote the phagocytic ability of macrophage, etc.) and/or specificity (specifically recognizes TTRs with structural change and TTR fibril), is useful as an effective medicament to various diseases associated with structural change or fibrillization of TTR.

The invention claimed is:

1. A humanized antibody having the activity to inhibit fibrillization of transthyretin (TTR) which binds to TTR amyloid derived from two or more kinds of variant TTRs and wherein the variant TTR is TTR having a mutation selected from the group consisting of D18G, V30M, E54K, L55P, Y114C, Y116S and V122I, the antibody comprising a complementarity determining region (CDR) of a heavy chain comprising the polypeptide of (a) or (b) below and a CDR of a light chain comprising the polypeptide of (c) or (d) below:
   (a) a polypeptide comprising the complementarity determining regions (CDRs) of SEQ ID NOs: 1 to 3;
   (b) a polypeptide comprising SEQ ID NO: 7;
   (c) a polypeptide comprising the CDRs of SEQ ID NOs: 4 to 6;
   (d) a polypeptide comprising SEQ ID NO: 8.

2. The humanized antibody of claim 1 which specifically recognizes TTRs with structural change.

3. The humanized antibody of claim 1 which specifically binds to TTR amyloid.

4. The humanized antibody of claim 1 which promotes removal of TTR amyloid.

5. The humanized antibody of claim 1 which promotes the phagocytic ability of macrophages to TTR amyloid.

6. The humanized antibody of claim 1 wherein an epitope is a sequence comprising position 118 to position 122 of TTR.

7. The humanized antibody of claim 6 wherein an epitope is position 118 to position 122 of TTR.

8. The humanized antibody of claim 1 which has a therapeutic effect to TTR amyloidosis.

9. The humanized antibody of claim 8 wherein the TTR amyloidosis is Familial Amyloidotic Polyneuropathy (FAP).

10. The humanized antibody of claim 8 wherein the TTR amyloidosis is Senile Systemic Amyloidosis (SSA).

11. The humanized antibody of claim 1, which is formed by linking a human-derived constant region to:
   (1) a heavy chain variable region fragment comprising a complementarity determining region of a heavy chain comprising the CDRs of SEQ ID NOs: 1 to 3;
   or
   (2) a heavy chain variable region fragment comprising a complementarity determining region of an H chain comprising SEQ ID NO: 7;
   and
   (3) a light chain variable region fragment comprising a complementarity determining region of a light chain comprising the CDRs of SEQ ID NOs: 4 to 6;
   or (4) a light chain variable region fragment comprising a complementarity determining region of a light chain comprising SEQ ID NO: 8.

12. A TTR-fibrillization inhibitor comprising the antibody or a fragment thereof of claim 1.

13. A pharmaceutical composition for the treatment of TTR amyloidosis comprising the antibody or a fragment thereof of claim 1.

14. The pharmaceutical composition of claim 13 wherein the TTR amyloidosis is Familial Amyloidotic Polyneuropathy (FAP).

15. The pharmaceutical composition of claim 13 wherein the TTR amyloidosis is Senile Systemic Amyloidosis (SSA).

16. A single-chain variable region fragment of an antibody to TTR, which is formed by linking:
   a) a heavy chain variable region fragment comprising the complementarity determining regions (CDRs) comprising SEQ ID NOs: 1 to 3,
   or
   b) a heavy chain variable region fragment comprising the CDRs comprising SEQ ID NO: 7,
   and
   c) a light chain variable region fragment comprising the CDRs of SEQ ID NOs: 4 to 6,
   or
   d) a light chain variable region fragment comprising the CDRs comprising SEQ ID NO: 8.

\* \* \* \* \*